United States Patent
Singh et al.

(10) Patent No.: US 11,945,833 B2
(45) Date of Patent: Apr. 2, 2024

(54) PRODRUGS OF L-BHDU AND METHODS OF TREATING VIRAL INFECTIONS

(71) Applicants: UNIVERSITY OF GEORGIA RESEARCH FOUNDATION, INC., Athens, GA (US); Anterogen Co., Ltd, Seoul (KR)

(72) Inventors: Uma Sharan Singh, Athens, GA (US); Chung Chu, Duluth, GA (US)

(73) Assignees: University of Georgia Research Foundation, Inc., Athens, GA (US); Anterogen Co., Ltd., Seoul (KR)

( * ) Notice: Subject to any disclaimer, the term of this patent is extended or adjusted under 35 U.S.C. 154(b) by 0 days.

(21) Appl. No.: 17/976,407

(22) Filed: Oct. 28, 2022

(65) Prior Publication Data

US 2023/0167143 A1 Jun. 1, 2023

Related U.S. Application Data

(60) Provisional application No. 63/273,403, filed on Oct. 29, 2021.

(51) Int. Cl.
| | |
|---|---|
| C07F 9/6558 | (2006.01) |
| A61K 31/675 | (2006.01) |
| A61K 45/06 | (2006.01) |
| A61P 31/22 | (2006.01) |

(52) U.S. Cl.
CPC ........ *C07F 9/65586* (2013.01); *A61K 31/675* (2013.01); *A61K 45/06* (2013.01); *A61P 31/22* (2018.01)

(58) Field of Classification Search
CPC .................................................. C07F 9/65586
See application file for complete search history.

(56) References Cited

PUBLICATIONS

De C; et al. Beta-L-1-[5-(E-2-bromovinyl)-2-(hydroxylmethyl)-1,3-(dioxolan-4-yl)] uracil (L-BHDU) prevents varicella-zoster virus replication in a SCID-Hu mouse model and does not interfere with 5-fluorouracil catabolism. Antiviral research, 2014;110:10-19.
Rautio J; et al. The expanding role of prodrugs in contemporary drug design and development. Nature reviews drug discovery, 2018;17:559-587.
Heidel KM; et al. Phosphonate prodrugs: an overview and recent advances. Future medicinal chemistry, 2019;11(13):1625-1643.
Pradere U; et al. Synthesis of nucleoside phosphate and phosphonate prodrugs. Chemical reviews, 2014;114:9154-9218.
Chol Y; et al. Structure-activity relationships of (e)-5-(2-bromovinyl)uracil and related pyrimidine nucleosides as antiviral agents for herpes viruses. Journal of medicinal chemistry, 2000;43:2538-2546.
Search Report for PCT/US2022/048241, dated Jul. 2022.
Noble S; Goa KL. Adefovir Dipivoxil. Drugs; 1999;58(3):479-487.
Naesens L, et al. HPMPC (cidofovir), PMEA (adefovir), and related acyclic nucleoside phosphonate analogues: a review of their pharmacology and clinical potential in the treatment of viral infections. Antiviral Chemistry & Chemotherapy, 1997;8(1):1-23.
Serafim Ram, et al. Chemical Probes for Understudied Kinases: Challenges and Opportunities. J. Med. Chem. 2022;65:1132-1170.
Dando TM, Plosker GL. Adefovir Dipivoxil A Review of its Use in Chronic Hepatitis B. Drug, 2003;63(20):2215-2234.
Cullen JM, et al. Antiviral Efficacy and Pharmacokinetics of Oral Adefovir Dipivoxil in Chronically Woodchuck Hepatitis Virus-Infected Woodchuck. Antimicrobial Agents and Chemotherapy, 2001;2740-2745.

*Primary Examiner* — Rei Tsang Shiao
(74) *Attorney, Agent, or Firm* — Henry D. Coleman; R. Neil Sudol

(57) ABSTRACT

In an embodiment, the invention is directed to prodrug compounds of L-BHDU according to the chemical structure I:

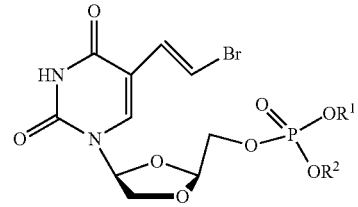

Where $R^1$ is a $—(CH_2)_n—O—R^{1a}$ group or a $—(CH_2)_j—O—C(O)O_k—R^{2a}$ group;
$R^2$ is H, a $—(CH_2)_n—O—R^{1a}$ group or a $—(CH_2)_j—O—C(O)O_k—R^{2a}$ group;
$R^{1a}$ is independently a $C_6$-$C_{30}$ alkyl group, often a $C_{12}$-$C_{22}$ alkyl group, often a $C_{14}$-$C_{20}$ alkyl group or a $C_{16}$-$C_{18}$ alkyl group, often a $C_{16}$ or $C_{18}$ alkyl group;
$R^{2a}$ is independently a $C_1$-$C_{12}$ alkyl group, often a $C_2$-$C_6$ alkyl group, a $C_3$-$C_4$ alkyl group, an isopropyl, t-butyl or sec-butyl group, or an isopropyl or t-butyl group;
Each j is independently 1-6, 1-3, often 1 or 2;
Each k is 0 or 1;
Each n is independently 1-6, 1-4, 2-4 or 2 or 3; or
A pharmaceutically acceptable salt, solute or polymorph thereof. Additional embodiments are directed to pharmaceutical compositions based upon the disclosed chemical compounds and methods of treating or reducing the likelihood of VZV, HSV-1 or HSV-2 infections. Methods of synthesizing compounds according to the present invention represent further embodiments of the invention.

42 Claims, 16 Drawing Sheets

Scheme 1

Scheme 2

Scheme 3

Synthesis of bis POC-L-BDHU prodrug

FIGURE 5

Table 1. Anti-VZV activity in ARPE-19 cells

| Compounds | $EC_{50}$ (µM)[a] (mean±SD) | $CC_{50}$ (µM)[b] | SI ($CC_{50}/EC_{50}$)[c] |
|---|---|---|---|
| L-BHDU | 0.022 ± 0.008 | >100 | >4456 |
| OED-L-BHDU (5) | 0.068 ± 0.0005 | 32.5 | 479 |
| HDP-L-BHDU (6) | 0.090 ±0.0006 | 10 | 111 |
| POM-L-BHDU (8) | 0.028 ± 0.006 | >100 | >3619 |
| POC-L-BDHU (14) | 0.034 ± 0.009 | >100 | >2915 |

[a] 50% inhibitory concentration 48 hpi determined by bioluminescence imaging, mean ± standard deviation from at least 3 experiments.
[b] 50% cytotoxic concentration at 72 h determined by neutral red assay from 3 experiments.
[c] Selectivity index.

FIGURE 9

Table 2. Anti-HSV-1 activity of L-BHDU prodrugs in Vero Cells.

| Compounds | $EC_{50}$ (μM) (mean±SD) | $CC_{50}$ (μM) | SI ($CC_{50}/EC_{50}$) |
|---|---|---|---|
| L-BHDU | 0.007 | >100 | >12,903 |
| OED-L-BHDU | 0.7553 | 20 | 26 |
| POM-L-BHDU | 0.0282 | >100 | >3,546 |
| POC-L-BDHU | 0.0260 | >100 | >3,846 |
| Acyclovir (ACV) | 0.0736 | ND | ND |

ND : Not Determined.

FIGURE 11

Table 3. Anti-HSV-2 activity in Vero Cells.

| Compounds | EC$_{50}$ (µM) (mean±SD) | CC$_{50}$ (µM) | SI (CC$_{50}$/EC$_{50}$) |
|---|---|---|---|
| L-BHDU | n/a | >100 | -- |
| OED-L-BHDU | n/a | 20 | -- |
| POM-L-BHDU | 1.4 | >100 | >71 |
| POC-L-BDHU | n/a | >100 | -- |
| Acyclovir | 0.99 | ND | ND | n/a : no activity; ND: Not Determined

FIGURE 14

Table 4. Antiviral activity of L-BHDU and several prodrugs against cell-associated wild-type and mutant VZV viruses in ARPE-19 cells.

| Viral Strains | $EC_{50}$ (μM) | | | | | |
|---|---|---|---|---|---|---|
| | CDV | ACV | L-BHDU | POM-L-BHDU | POC-L-BHDU | ODE-L-BHDU |
| VZV-ORF57-Luc | 0.37 | 7.75 | 0.18 | 0.051 | 0.040 | 0.82 |
| VZV-ORF57-ΔTK | 0.42 | >20 | >2.0 | >2.0 | >2.0 | >2.0 |
| VZV-ORF57-ΔTS | 0.01 | 0.37 | 0.028 | 0.0012 | 0.0084 | 0.0008 |
| VZV-ORF57-ΔTKTS | 1.05 | >20 | >2.0 | >2.0 | >2.0 | >2.0 |

PRODRUGS OF L-BHDU AND METHODS OF TREATING VIRAL INFECTIONS

FIELD OF THE INVENTION

The present invention is directed to prodrug compounds of β-L-[5-(E-2-bromovinyl)-2-(hydroxymethyl)-1,3-(dioxolane-4-yl) uracil (L-BHDU), pharmaceutical compounds thereof, and methods of treatment against the Varicella Zoster Virus (VZV) and Herpes Simplex Viruses. (HSV-1 &2). Methods of synthesizing these compounds are also disclosed.

RELATED APPLICATIONS

This application claims the benefit of priority of provisional application Ser. No. U.S. 63/273,403, filed Oct. 29, 2021, the entire contents of which is incorporated by reference herein.

Background and Overview of the Invention Varicellazoster virus (VZV) causes chickenpox (varicella) on primary infection and shingles (zoster) upon the reactivation at the latency stage in humans.[1] VZV belongs to the y herpes family and is partially curable by the live inoculation with the attenuated vaccine strain Oka-Merck.[2] However, pediatric vaccination has reduced chickenpox cases, but shingles remain challenging in elderly age persons. In the older person, the efficacy of the vaccine reduces approximately 50%, which quickly leads to reinfection and creates a painful shingle condition. Postherpetic neuralgia is one of the major complications of shingles.[3] It is characterized by skin rash due to reactivation of VZV with a persistent pain. Due to natural and breakthrough cases of VZV, immunocompromised patients cannot receive the vaccine. Therefore, the course of varicella easily begins in the immunocompromised patients, especially patients suffering from acquired immune deficiency syndrome (AIDS), transplant recipients, and cancer patients. In these conditions, VZV infection can be life-threatening.

The current treatments of nucleoside drug analogs are acyclovir (ACV), valaciclovir (VACV), and famciclovir.[4] However, these drugs show low efficacy and low bioavailability, and long-term uses of these therapies are associated with drug resistance. In drug-resistant patients, foscarnet (phosphonoformate) is administered intravenously to treat the resistant VZV, which is associated with many side effects and cytotoxicity.[5] The available nucleoside drugs act on the viral DNA polymerase in the active triphosphate form and mimic viral replication. Cellular enzymes like thymidine kinase (TK) and cellular kinase (CK) convert nucleoside drugs into active triphosphate moiety.[6] The cyclic derivatives of uridine, another class of compounds, have been invented to treat the VZV. Herpes zoster ophthalmicus (eye infection) may be treated with topical trifluridine and idoxuridine.[7] First, bromo vinyl analog, brivudine (BVDU, E-5-(2-bromovinyl)-2'-deoxy uridine showed better anti-herpes activity and is approved in Europe for the treatment of VZV infections.[8] Similarly, BVDU also converts into the 5'-monophosphate and 5'-diphosphate form by the viral TK enzyme, which ultimately converts into 5'-triphosphonate (BVDU-TP) form by the cellular kinases. BVDU-TP selectively interacts with the viral DNA polymerase either in the form of the competitive inhibitor or incorporated into the DNA chain and leads to the DNA chain termination. BVDU has demonstrated a better activity profile than acyclovir and its derivatives. Additionally, easy dosing of BVDU makes it more appealing among elderly patients than other drugs used for VZV infection. The major drawback associated with this drug is that during the metabolism, it cleaves into BVD metabolites. BVD inhibits dihydropyridine dehydrogenase, which is essential for the degradation of the thymidine and uracil. Therefore, cancer patients being treated with 5-fluoro uracil (5-FU) cannot be administrated with BVDU because the use of BVDU will cause the accumulation of the toxic 5-FU in these patients and result in early death.[9] Due to described drawbacks and significant adverse effects of currently prescribed drugs, there is great demand for new antiviral drugs that can hamper the spread of VZV in the skin, especially since the approved drugs have little to no effect on the growth of the virus.

Therefore, there is a continuous demand for new antiviral drugs against the VZV. To deal with the current challenges of VZV treatments, the inventors have developed the uridine derivative β-L-[5-(E-2-bromovinyl)-2-(hydroxymethyl)-1,3-(dioxolane-4-yl) uracil (L-BHDU).[10] L-BHDU in vitro expressed an $EC_{50}$ value of 0.22 µM against VZV in the human foreskin fibroblast (HFFS) cells. It was also found non-cytotoxic to cells at 200 µM concentration and revealed a selective index (SI) of >909.[11] To increase the cellular bioavailability and cell uptake of L-BHDU, amino prodrugs of L-BHDU were synthesized. Out of these amino prodrugs, L-valyl-L-BHDU demonstrated an enhanced antiviral activity with an $EC_{50}$ value of 0.03 µM and $CC_{50}$ of 200 µM with SI of >6667. In vivo studies of L-BHDU and L-valyl-L-BHDU show a significant reduction in VZV growth compared to ACV and VACV. Furthermore, L-BHDU studies indicated that it does not inhibit the activity of dihydropyridine dehydrogenase.[11] Thus, the cancer-treating patients with 5-FU can also be administrated with L-BHDU.

Encouraged by these findings, the inventors were keen to explore various prodrug approaches to improve the antiviral potency of L-BHDU against VZV. In this application, the synthesis and antiviral evaluation of the POM, POC, octadecyl, and hexadecyl prodrugs of L-BHDU is described. It has been proved that both POM and POC groups have shown an increase in bioavailability and make easy access to the conversion of the active triphosphate form of the parental nucleoside.[12] To date, the US FDA has approved adefovir dipivoxil [bis(pivaloyloxymethyl), POM][13, 14] for HBV and tenofovir disoproxil fumarate [bis(isopropyloxymethyl carbonate, POC][15] for HIV treatment. In the metabolism of POM prodrugs, first POM ester group degrades and forms an unstable hydroxymethyl alcoholate intermediate which undergoes chemical rearrangement and releases formaldehyde. After the second POM ester group cleavage generates free monophosphate.[16] Similarly, POC prodrugs also metabolize via enzymatic degradation. Carbonates of POC decompose by esterase and produce unstable carboxylate intermediate that, on the sequential release of carbon dioxide, followed by formaldehyde produces free nucleotide monophosphate. Considering these frequent conversion of nucleoside to monophosphate form, POM (8) and POC (14) prodrugs (FIGS. 2 and 3, respectively) of L-BHDU were synthesized and evaluated in vitro and in vivo against VZV. These prodrugs have demonstrated a better in vitro and in vivo activity in comparison to L-BDHU. Furthermore, POM-L-BHDU was selected for further in vivo evaluation where this prodrug demonstrated better activity compared to parental molecule.

It is proven that the 1-O-hexadecyloxypropyl and 1-O-octadecyloxyethyl of cidofovir have shown enhanced activity against the cytomegalovirus and herpesvirus. These prodrugs inhibit viral replication more efficiently compare to cidoforvir.[17] These long-chain lipid prodrug also show improved cell absorption and oral bioavailability. However, we are targeting the nerve cells which dominantly become infected by the VZV. Hence, a more lipophilic nature of the L-BHDU was required. To increase the lipophilicity and cell bioavaliablity of the L-BHDU, octadecyloxyethyl-L-BHDU (ODE-L-BHDU, 5) and hexadecyloxypropyl-L-BHDU (HDP-L-BHDU, 6), FIG. 1, Scheme 1 were synthesized and screened in vitro and in vivo for antiviral activity. Esterification of L-BHDU with octadecyloxyethyl (ODE) and hexadecyloxypropyl (HDP) was implied to design to increase the cellular uptake of L-BHDU based phospholipids/lipophilic function of the cell membrane. The addition of these long hydrocarbon chains may lead to potential improvement for intracellular transportation of the compounds. However, for these analogs, enhanced in vitro antiviral activity was unexpected. As predicated, in vitro HDP-L-BHDU and ODE-L-BHDU have expressed lower antiviral activity relative to L-BHDU. Furthermore, ODE-L-BHDU (5) was selected for the in vivo studies where this prodrug has demonstrated better antiviral activity in comparison to L-BHDU.

Varicella-zoster virus (VZV) is an alphaherpes virus that causes chickenpox and shingles. Acyclovir and its prodrugs, brivudine (BVdU), and foscarnet are the currently prescribed drugs against the VZV infection. There is still a need of new antiviral drugs with enhanced potency and specificity to treat VZV, especially to treat post-herpetic neuralgia. We showed that β agent is an anti-cancer compound. In other embodiments, the additional bioactive agent is 5-Fluorouracil (5FU).

In embodiments, the invention is directed to methods of treating, inhibiting or reducing the likelihood of a Varicella Zoster Virus (VZV) infection or Herpex Simplex (HSV I and II) infections or complications thereof comprising administering to a patient in need an effective amount of a compound as described herein. In embodiments, the infection is a VZV infection (chicken pox or shingles). In embodiments, the infection is a herpes simplex virus I or II infection (HSV-1 or HSV-2). In embodiments, the method of treatment utilizes a combination of agents, often a prodrug of L-BHDU as described herein and an optional additional bioactive agent as described herein which are co-administered to a patient or subject in need.

In embodiments, the invention provides methods of synthesizing compounds according to the present invention as described herein.

BRIEF DESCRIPTION OF THE FIGURES

FIG. 5, Table 1 shows the anti-VZV activity of compounds in ARPE-19 cells. In this assay, L-BHDU was found 10-fold more potent than in the previous assay using HFFs infected with VZV-BAC-Luc (0.22 μM in HFFs, 22 nM in ARPE-19s).[11] L-BHDU revealed a good antiviral potency $EC_{50}$ of 0.022 μM

FIG. 9, Table 2 presents the anti-HSV-1 activity data of L-BHDU prodrugs in Vero Cells.

FIG. 14, Table 4 shows the antiviral activity of L-BHDU and several prodrugs against cell-associated wild-type and mutant VZV viruses in ARPE-19 cells.

DETAILED DESCRIPTION OF THE INVENTION

Figure 1:
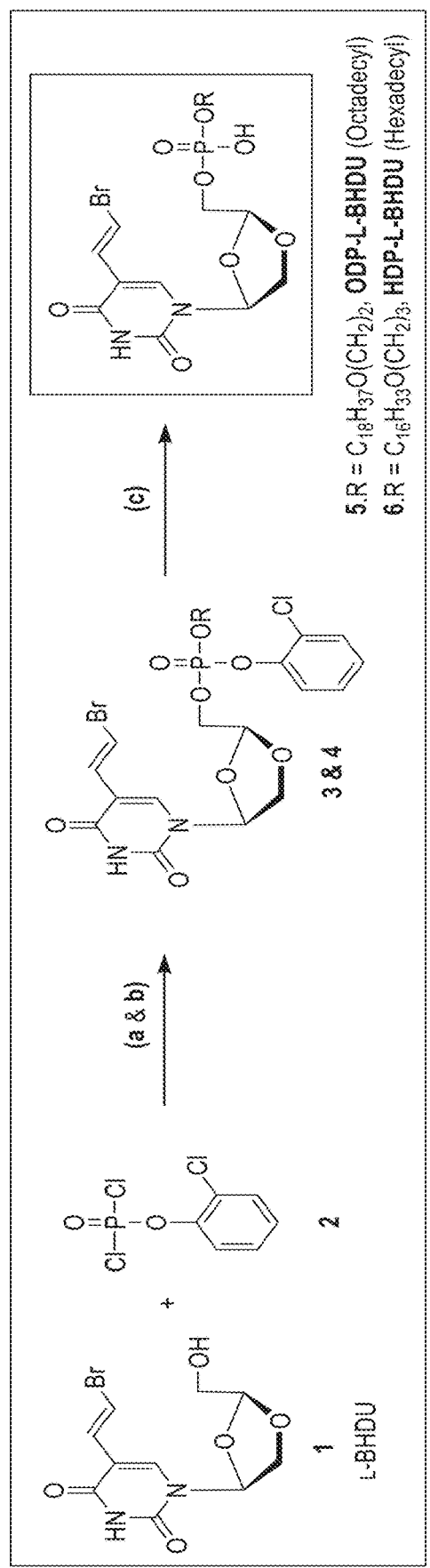
FIG. 1, Scheme 1 shows the chemical synthesis of long chain lipid phosphate of L-BDHU, compounds 5 and 6. Reagent and Conditions: (a) 1,2,4-triazole, $Et_3N$, THF, rt; (b) ROH, N-methylimidazole (NMI), THF, rt; (c) 0.5N NaOH, $THF/H_2O$, 50° C.

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents which form stable bonds are to be used.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

The term "compound", as used herein, unless otherwise indicated, refers to any specific chemical compound disclosed herein, generally refers to prodrug forms of β-L-[5-(E-2-bromovinyl)-2-(hydroxymethyl)-1,3-(dioxolane-4-yl) uracil (L-BHDU) as disclosed herein, but may include, within context, tautomers, regioisomers, geometric isomers, anomers, and where applicable, optical isomers (enantiomers) or diastereomers (two chiral centers) thereof of these compounds, as well as pharmaceutically acceptable salts thereof, solvates and/or polymorphs thereof. Within its use in context, the term compound generally refers to a single compound, but also may include other compounds such as stereoisomers, regioisomers and/or optical isomers (including racemic mixtures and/or diastereomers as described herein) as well as specific enantiomers, enantiomerically enriched or individual diastereomers or mixtures of disclosed compounds, depending on the context of the term's use. It is noted that in the event that a carbon range is provided for a compound, that range signifies that each and every carbon individually is considered part of the range. For example, a $C_1$-$C_{20}$ group describes a group with a single carbon, two carbon atoms, three carbon atoms, four carbon atoms, etc. up to twenty carbons.

The term " "patient or "subject" is used throughout the specification to describe an animal, often a domesticated animal or a human, more often a human to whom treatment, including prophylactic treatment, with the compositions according to the present invention is provided. For treatment of those infections, conditions or disease states which are specific for a specific animal such as a human patient, the term patient refers to that specific animal. In general, in the present invention, the term patient refers to a human patient unless otherwise stated. In the present invention, in addition to humans, domesticated animals (e.g., horses, cows, dogs, cats, etc.) also may be treated with compounds according to the present invention.

The term "Varicella Zoster virus" or "VZV" is used to describe one of eight herpes viruses known to infect humans (and other vertebrates). VZV commonly causes chicken-pox in children and both shingles and postherpetic neuralgia in adults. Varicella-zoster virus is known by many names, including: chickenpox virus, varicella virus, zoster virus, and human herpes virus type 3 (HHV-3). Primary VZV infection results in chickenpox (varicella), which may rarely result in complications including encephalitis or pneumonia. Even when clinical symptoms of chickenpox have resolved, VZV remains dormant in the nervous system of the infected person (virus latency), in the trigeminal and dorsal root ganglia. In about 10-20% of cases, VZV reactivates later in life producing a disease known as herpes zoster or shingles.

Serious complications of shingles include postherpetic neuralgia, zoster multiplex, myelitis, herpes ophthalmicus, or zoster sine herpete. Compounds according to the present invention are useful to inhibit, treat or resolve complications associated with these viral infections.

VZV is closely related to the herpes simplex viruses (HSV I and II), sharing much genome homology. Many of the known envelope glycoproteins of VZV correspond with those in HSV. VZV, unlike HSV, fails to produce the LAT (latency-associated transcripts) that play an important role in establishing HSV latency (herpes simplex virus). The virus is very susceptible to disinfectants, notably sodium hypochlorite. Within the human body, along with compounds of the present invention, it can be treated by a number of drugs and therapeutic agents including acyclovir, zoster-immune globulin (ZIG), and vidarabine.

The term "Herpes simplex virus", "Herpes simplex virus-1" (HSV-1), "Herpes simplex virus-2" (HSV-2), are two species of the herpes virus family, Herpesviridae, which cause infections in humans. As with other herpesviridae, herpes simplex virus may produce life-long infections. They are also called Human Herpes Virus 1 and 2 (HHV-1 and HHV-2) and are neurotropic and neuroinvasive viruses; they enter and hide in the human nervous system, accounting for their durability in the human body. HSV-1 is commonly associated with herpes outbreaks of the face known as cold sores or fever blisters, whereas HSV-2 is more often associated with genital herpes, although each of the two strains of HSV may be found in areas normally associated with the other strain.

An infection by a herpes simplex virus is marked by complications or symptoms of watery blisters in the skin or mucous membranes of the mouth, lips or genitals. Lesions heal with a scab characteristic of herpetic disease. However, the infection is persistent and symptoms may recur periodically as outbreaks of sores near the site of original infection. After the initial, or primary, infection, HSV becomes latent in the cell bodies of nerves in the area. Some infected people experience sporadic episodes of viral reactivation, followed by transportation of the virus via the nerve's axon to the skin, where virus replication and shedding occurs. Herpes is contagious if the carrier is producing and shedding the virus. This is especially likely during an outbreak but possible at other times. There is no cure yet, but there are treatments which reduce the likelihood of viral shedding.

The term "pharmaceutically acceptable salt" is used throughout the specification to describe, where applicable, a salt form of one or more of the compounds described herein which are presented to increase the solubility of the compound often in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of the phosphates according to the present invention. Other salts such as base addition salts may also be used in certain embodiments.

The term "pharmaceutically acceptable derivative" is used throughout the specification to describe any pharmaceutically acceptable prodrug form of the present invention which, upon administration to a patient, provides directly or indirectly L-BHDU or an active metabolite of L-BHDU.

The term "alkyl" shall mean within its context a $C_1$-$C_{30}$, preferably a $C_1$-$C_{20}$ linear, branch-chained or cyclic, often linear or branch-chained fully saturated hydrocarbon radical. It is noted that in the event that a carbon range is provided, that range signifies that each and every carbon is considered part of the range. For example a $C_1$-$C_{20}$ group describes a group with a single carbon, two carbon atoms, three carbon atoms, four carbon atoms, etc. The term "ether" shall mean an optionally substituted $C_1$ to $C_{20}$ ether group, formed from an oxygen and an alkyl group, or alternatively, may also contain at least one oxygen within the alkyl or alkylene chain.

The term "effective amount" shall mean an amount or concentration of a compound according to the present invention which is effective within the context of its administration or use, which may be inhibitory, prophylactic and/or therapeutic. Within context, all active compounds which are used in the present invention are used in effective amounts. The present compound also relates to combinations of compounds which contain effective amounts of each of the compounds used, whether that combination is additive or synergistic in effect, provided that the overall effect of the combination of compounds is to inhibit the growth, reduce the likelihood of or treat viral infections in patients as otherwise described herein.

The term "L-configuration" as used in the context of the present invention refers to the configuration of the nucleoside compounds according to the present invention which mimics the unnatural configuration of sugar moeties as opposed to the natural occurring nucleosides or "D" configuration. The term "β" or "β anomer" is used to describe nucleoside analogs according to the present invention in which the nucleoside base is configured (disposed) above the plane of the dioxolane moiety in the compound.

The term "enantiomerically enriched" is used throughout the specification to describe a nucleoside which includes at least about 95%, preferably at least about 96%, more preferably at least about 97%, even more preferably, at least about 98%, and even more preferably at least about 100% or more of a single enantiomer of that nucleoside. Prodrug L-BHDU nucleoside compounds according to the present invention are generally β-L-nucleoside compounds. When the present compounds according to the present invention are referred to in this specification, it is presumed that the nucleosides have the L-nucleoside configuration and are enantiomerically enriched (preferably, approximately 100% of the L-nucleoside), unless otherwise stated. The term "diasteromerically pure" is used to describe a single diastereomer of a compound according to the present invention which contains at least 95%, 96%, 97%, 98%, 99%, 99.5% or 100% by weight of a single diastereomer to the inclusion of other possible diastereomers.

The terms "coadminister" and "coadministration" are used synonymously to describe the administration of at least one of the nucleoside compounds according to the present invention in combination with at least one other agent, preferably at least one additional anti-viral agent, including other nucleoside anti-viral agents which are specifically disclosed herein in amounts or at concentrations which would be considered to be effective amounts at or about the same time. While it is preferred that coadministered agents be administered at the same time, agents may be administered at times such that effective concentrations of both (or more) agents appear in the patient at the same time for at least a brief period of time. Alternatively, in certain aspects of the present invention, it may be possible to have each coadministered agent exhibit its inhibitory or therapeutic effect at different times in the patient, with the ultimate result being the inhibition of the virus and the treatment of the aforementioned infections. Of course, when more than one viral or other infection or other condition is present, the present compounds may be combined with agents to treat that other infection or condition as required. In certain preferred compositions and methods, the present L-BHDU prodrug compounds are coformulated and/or coadministered with at least one additional antiviral agent, preferably wherein the antiviral agent is acyclovir, famciclovir, ganciclovir, valaciclovir, vidaribine, foscarnet, zoster-immune globulin (ZIG) and mixtures thereof. Coadministration with 5-fluorouracil (5-FU) is also contemplated by the present invention.

The term "independently" is used herein to indicate that the variable, which is independently applied, varies independently from application to application.

The present invention also relates to pharmaceutical compositions comprising an effective amount of a compound as described above, optionally in combination with a pharmaceutically acceptable carrier, additive or excipient. In alternative embodiments, pharmaceutical compositions may also contain one or more additional antiviral agents as otherwise described herein in combination with an additive, carrier or excipient.

Methods of treatment represent further embodiments according to the present invention. In this aspect, a method of treating or reducing the likelihood of a viral infection or a secondary disease state or condition thereof, in particular, a viral infection from VZV, HSV-1 or HSV-2 infection in a patient in need of therapy or at risk for infection or a secondary disease state or condition thereof comprises administering to said an effective amount of a compound or composition as otherwise described above. Alternative embodiments rely on coadministering compounds according to the present invention in combination with additional antiviral agents to said patient. In preferred aspects, a method of treating or reducing the likelihood of VZV or HSV-1 or HSV-2, including a drug resistant strain thereof or a secondary disease or condition which occurs as a consequence of VZV, HSV-1 or HSV-2 is directed to administering to a patient in need an effective amount of compound according to the present invention as described herein, or a pharmaceutically acceptable salt, solvate or polymorph thereof.

Pharmaceutical compositions based upon the nucleoside compounds according to the present invention comprise one or more of the above-described compounds in an effective amount for treating or reducing the likelihood of a viral infection, especially a VZV, HSV-1, or HSV-2 infection in a patient in need of therapy thereof, optionally in combination with a pharmaceutically acceptable additive, carrier or excipient. One of ordinary skill in the art will recognize that a therapeutically effective amount will vary with the infection or condition to be treated, its severity, the treatment regimen to be employed, the pharmacokinetics of the agent used, as well as the patient or subject (animal or human) to be treated.

In the pharmaceutical aspect according to the present invention, the compound according to the present invention is formulated preferably in admixture with a pharmaceutically acceptable carrier. In general, it is preferable to administer the pharmaceutical composition in orally-administrable form, but certain formulations may be administered via a parenteral, intravenous, intramuscular, transdermal, buccal, intranasal, subcutaneous, inhalation, suppository or other route. Intravenous and intramuscular formulations are often administered in sterile saline. In certain instances, topical or transdermal administration may be used. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms mono-phosphate esters and various salt forms of the present compounds, may be preferred. In embodiments, phosphodiesters and triesters are used. One of ordinary skill in the art will recognize how to readily modify the present compounds to enhance the pro-drug compounds according to the present invention to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

The amount of compound included within active formulations according to the present invention is an effective amount for treating the infection or condition, especially a viral infection as otherwise described herein. In general, a therapeutically effective amount of the present compound in pharmaceutical dosage form usually ranges from about 0.05 mg/kg to about 100 mg/kg per day or more, more preferably, slightly less than about 1 mg/kg to about 25 mg/kg per day of the patient or considerably more, depending upon the compound used, the condition or infection treated and the route of administration. The active nucleoside compound according to the present invention is often administered in amounts ranging from about 0.5 mg/kg to about 25 mg/kg per day of the patient, depending upon the pharmacokinetics of the agent in the patient. This dosage range generally produces effective blood level concentrations of active compound which may range from about 0.05 to about 100 micrograms/cc of blood in the patient. For purposes of the present invention, a prophylactically or preventive effective amount (i.e. an amount which is effective to reduce the likelihood of a patient at risk from contracting a viral infection) of the compositions according to the present invention falls within the same concentration range as set forth above for therapeutically effective amount and is often/usually the same as a therapeutically effective amount.

Administration of the active compound may range from continuous (intravenous drip) to up to several oral administrations per day (for example, once daily, or four times daily or Q.I.D.) or transdermal administration and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the bioavailability/pharmacokinetics of the particular agent chosen as well as the severity of disease in the patient and the size and weight of the patient. Oral dosage forms are particularly preferred as are topical dosage forms, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques to favorably influence the pharmacokinetics and/or bioavailability of administered drugs. The use of these dosage forms may significantly enhance the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside or other compounds used according to the present invention.

In particularly preferred embodiments according to the present invention, the compounds and compositions are used to treat, prevent, reduce the likelihood of or delay the onset of a viral infection as otherwise disclosed herein (VZV, HSV-1 or HSV-2). Preferably, to treat, prevent, reduce the likelihood of or delay the onset of these infections or disease states and/or conditions which occur secondary to these viral infections, the compositions will be administered in oral dosage form in amounts ranging from about 250 micrograms up to about 500 mg-1 gram or more at least once a day, up to four times a day. In embodiments, the compounds are formulated in sustained release form and administered less frequently. The present compounds are preferably administered orally, but often may be administered parenterally, topically or in suppository form.

In the case of the co-administration of the present compounds in combination with an another compound used to treat a viral infection, in particular, a viral infection such as a VZV, HSV-1 or HSV-2 infection, the amount of the prodrug nucleoside compound according to the present to be administered ranges from about 1 mg/kg of the patient to about 500 mg/kg or more of the patient or considerably more, depending upon the second agent to be co-administered and its potency against each of the viral infections to be inhibited, the condition or infection treated and the route of administration. In the case of coadministration, the other antiviral agent may be preferably administered in amounts ranging from about 100 µg/kg (micrograms per kilogram) to about 500 mg/kg. In certain preferred embodiments, these compounds may be preferably administered in an amount ranging from about 1 mg/kg to about 50 mg/kg or more (usually up to about 100 mg/kg), generally depending upon the pharmacokinetics of the two agents in the patient. These dosage ranges generally produce effective blood level concentrations of active compound in the patient. Typical antiviral agents which may be coadministered with compounds according to the present invention include acyclovir, famciclovir, ganciclovir, valaciclovir, vidaribine, zoster-immune globulin (ZIG), and mixtures thereof. 5-FU is also often coadministered with compounds according to the present invention.

The compounds according to the present invention, may advantageously be employed prophylactically to prevent or reduce the likelihood of a viral infection or to prevent or reduce the likelihood of the occurrence of clinical symptoms associated with the viral infection or to prevent or reduce the likelihood of the spread of a viral infection to another person. Thus, the present invention also encompasses methods for the prophylactic treatment of a VZV, HSV-1 or HSV-2 infection. In this aspect according to the present invention, the present compositions may be used to prevent, reduce the likelihood of and/or delay the onset of a viral infection or a virus related disease state or condition or the spread of infection to other people. This prophylactic method comprises administering to a patient in need of such treatment or who is at risk for the development of a VZV, HSV-1 or HSV-2 infection, including a virus related disease state or condition or an infected patient who wishes to prevent or reduce the likelihood of a viral infection from spreading to another person, an amount of a compound according to the present invention alone or in combination with another anti-viral effective for alleviating, preventing, reducing the likelihood of or delaying the onset of the viral infection. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient. In the case of compounds of the present invention for the prophylactic treatment of viral infections, these compounds may be administered within the same dosage range for therapeutic treatment (i.e., about 250 micrograms up to about 500 mg. or more from one to four times per day for an oral dosage form) as a prophylactic agent to prevent the proliferation of the viral infection or alternatively, to prolong the onset of or reduce the likelihood of a patient contracting a virus infection which manifests itself in clinical symptoms.

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

Chemistry

In general, compounds according to the present invention are synthesized readily from L-BHDU pursuant to schemes 1, 2 and 3, which are presented herein below. The skilled practitioner can readily adapt the specific synthetic steps in order to provide facile syntheses of all of the compounds which are disclosed herein without engaging in undue experimentation.

ODE-L-BHDU and HDP-L-BHDU

Octadecyloxyethyl-L-BHDU (ODE-L-BHDU, 5) and hexadecyloxypropyl-L-BHDU (HDP-L-BHDU, 6) prodrugs were synthesized according to the inventor's described protocol.[18] These long-chain lipid phosphates of L-BHDU were synthesized using the phosphotriester approach as shown in FIG. 1, Scheme 1. Synthesis of L-BHDU was carried out by our previously reported method.[10] L-BHDU was condensed with 2-chlorophenyl dichlorophosphate (2) in the presence of 1,2,4-triazole and triethylamine to provide the coupled intermediate. Without further purification, the intermediate was treated with long-chain lipid alcohol (3-hexadecyloxy-1-propanol or 2-octadecyloxy-1-ethanol) in the presence of N-methylimidazole (NMI) in THF to give the fully protected corresponding phosphotriesters (3 & 4) in 64% yield, which were isolated by flash chromatography in good yields. The phosphotriester (3 or 4) displayed two closely distinguished signals in the $^{31}$P NMR corresponding to the two diastereoisomers. The presence of diastereoisomers was also apparent from H NMR spectroscopy. To remove the 2-chlorophenyl groups, the phosphotriester was dissolved in THF and treated with 0.5 N NaOH at 50° C. for 1.5 h to give the target prodrugs 5 and 6 in approximately 85 to 90% yield.

POM-L-BHDU

Figure 2:
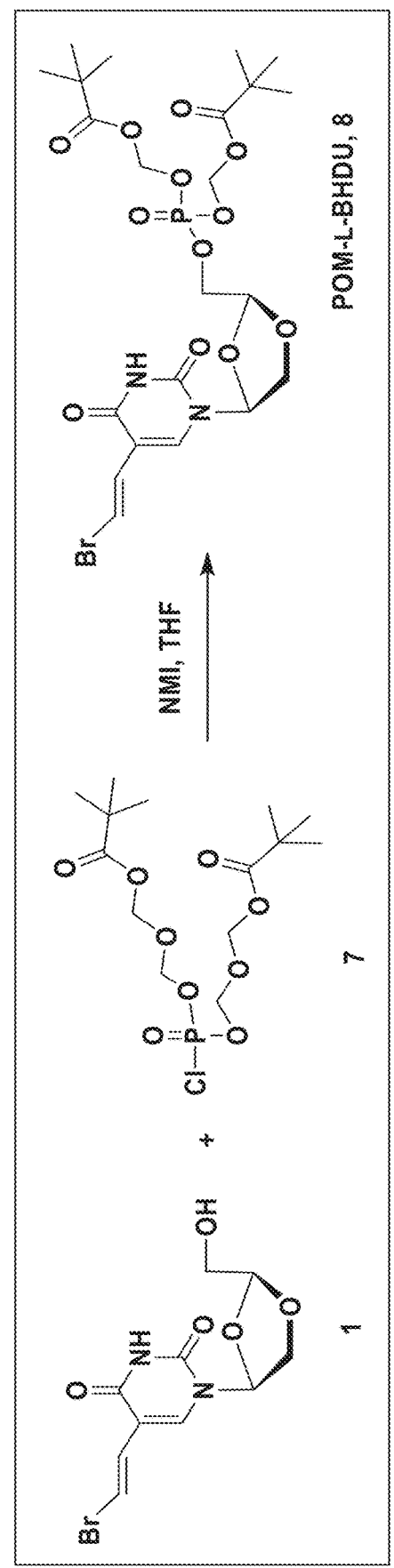
FIG. 2, Scheme 2 shows the chemical synthesis of POM-L-BHDU, compound 8. Reagent and Conditions: (a) NMI, THF, 0° C. to rt.

The synthesis of POM-L-BHDU is shown in FIG. 2, Scheme 2 and was initiated with the coupling of L-BHDU with chlorobis (POM) phosphate (7), as shown in scheme 2. Reagents and conditions for all chemical syntheses are disclosed in Brief Description of the FIGURES. Chlorobis (POM) phosphate (7) was synthesized according to the reported protocol of Hawang Y. et al.[19] L-BHDU was treated with 7 in the presence of the NMI in THF at 0° C. to rt to produce POM-L-BHDU in 71% yield.

Figure 3:
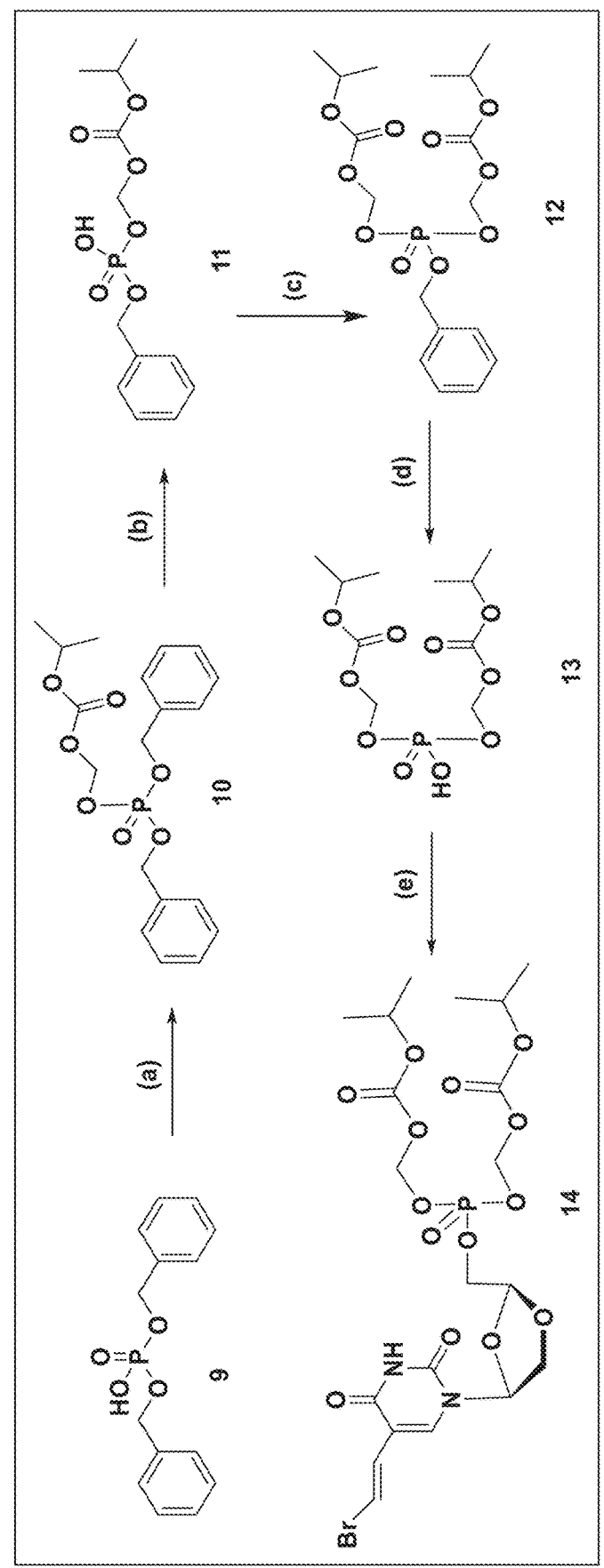
FIG. 3, Scheme 3 shows the chemical synthesis of bis POC-L-BDHU prodrug. Reagents and Conditions: (a) POC-I, $Cs_2CO_3$, acetone, rt, 24 h; (b) NaI, Acetonitrile, rt, 24 h; (c) POC-I, $Cs_2CO_3$, acetone, rt, 24 h (d) Pd/C, 5-10 psi, rt, 2 h (e) L-BHDU, BOP-Cl, 3-nitro-1, 2, 4-triazole, DIPEA, THF, rt, 2-3 h.

The synthesis of bis POC-L-BHDU (14) prodrug was commenced with compound 9. This is shown in FIG. 3, Scheme 3. The alkylation of 9 was carried out with the POC-I in cesium carbonate ($Cs_2CO_3$) in THF to give POC alkylated ester 10. Initially, the conversion of 10 to 11 was tried following the hydrogenation condition on Pd/C. In this attempt, selective mono benzyl deprotection was not achieved, and a major di-debenzylated product was obtained. Thus, selective mono benzyl deprotection was carried out with LiBr, but this conversion was very low yielding and only 7-9% of compound 11 was produced. Therefore, this reaction was revisited, and performed with the sodium iodide (NaI) in acetonitrile, in this case, it exclusively produces 11 in 92% yield. Repeated alkylation of 11 was accomplished by POC-I in the presence of $Cs_2CO_3$ in THP to give intermediate 12 in 70% yield. The final benzyl deprotection of 12 was executed on Pd/C in hydrogen at 5 psi to give key intermediate 13 in 85% yield. Intermediate 13 was coupled with the L-BDHU, in the presence of diisopropylamine (DIPEA), bis(2-oxo-3-oxazolidinyl)phosphinic chloride (BOP-Cl), and 3-nitro-1,2,4-triazole in THF at 0° C. to rt to furnish final Bis-POC-L-BHDU (14) in 22% yield. The identity of all the prodrugs was confirmed by ESI high-resolution mass spectra (ESI-HRMS), $^1$H-NMR, $^{13}$C-NMR, and $^{31}$P-NMR. These prodrugs were thereafter used in biological experiments described herein below.

Antiviral Activity

L-BHDU has antiviral activity against VZV and HSV-1. Antiviral potency of L-BHDU was tested in the SCID-Hu mouse model of VZV replication that employed human fetal skin and it was effective at 15 mg/kg.[11] L-BHDU was well tolerated up to 150 mg/kg and reached high levels in mouse organs but not in the brain. The antiviral activity of L-BHDU depends on phosphorylation by thymidine kinase encoded by VZV and HSV-1, and resistance maps to this gene.[20]

Figure 4:
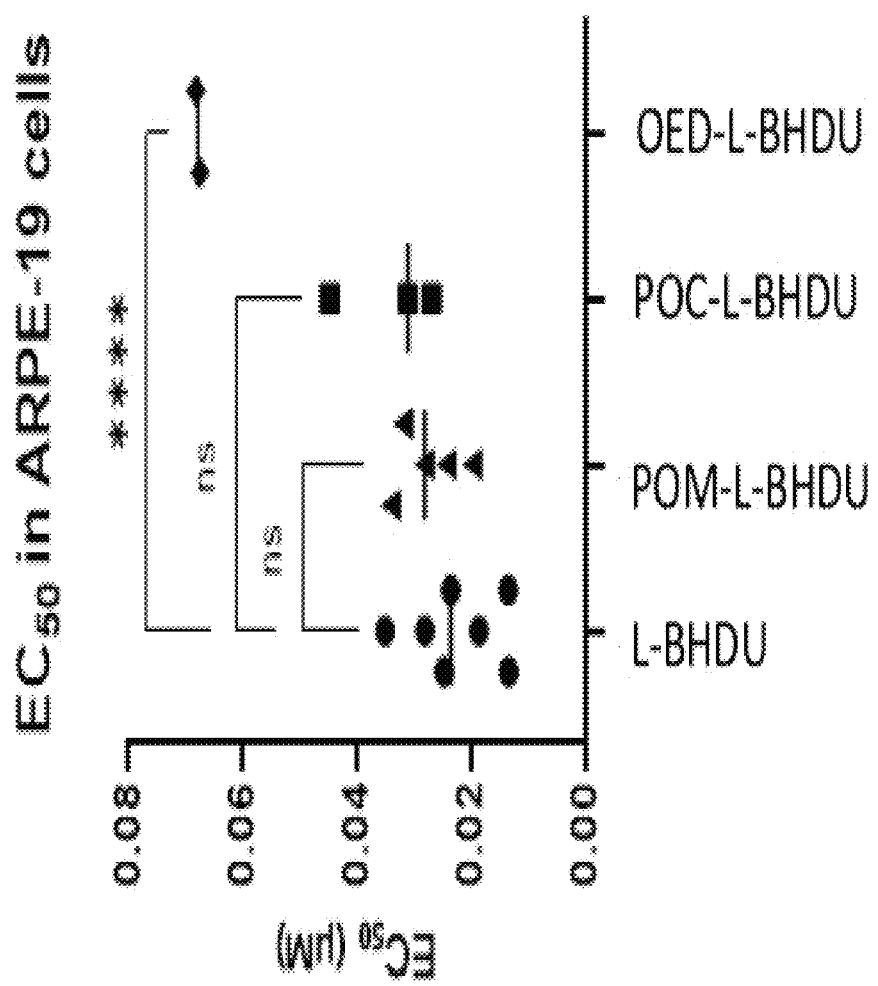
FIG. 4 shows a graph of the antiviral activity of L-BHDU and its prodrugs against VZV-BAC-Luc, in ARPE-19 cells.

To enhance the antiviral activity octadecyloxyethyl-L-BHDU (ODE-L-BHDU, 5) and hexadecyloxypropyl-L-BHDU (HDP-L-BHDU, 6), POM-L-BHDU (8), and POC-L-BDHU (14) (FIGS. 1-3, Schemes 1-3) prodrugs were synthesized with modifications to increase bioavailability and cell penetration. Their antiviral activity was evaluated in ARPE-19 cells infected with VZV-ORF57-Luc, a new reporter virus. In this assay, L-BHDU was found 10-fold more potent than in the previous assay using HFFs infected with VZV-BAC-Luc (0.22 μM in HFFs, 22 nM in ARPE-19s).[11] L-BHDU revealed a good antiviral potency $EC_{50}$ of 0.022 μM (See FIG. 4 and FIG. 5, Table 1). POM-L-BHDU and POC-L-BHDU analogs demonstrated good antiviral efficacy against VZV-ORF57-Luc, in ARPE-19 cells. POM-L-BHDU showed an $EC_{50}$ of 0.028 with a SI of 3619. This is similar to the antiviral efficacy of parental L-BHDU and POC-L-BHDU, which showed $EC_{50}$ of 0.034 μM with a SI of 2915. The long chain phospholipid prodrug OED-L-

BHDU (5) and HDP-L-BHDU (6) exhibited a $EC_{50}$ of 0.068 and 0.90 µM respectively with a SI of 479 & 111.

The cellular toxicity of synthesized analogs was determined on low passage of human fibroblast (HFFs) cells by performing 72 h of neutral red dye uptake and MTT cell proliferation assays. L-BHDU and its POM and POC prodrugs were found noncytotoxic ($CC_{50}$>100 µM) and did not affect cellular proliferation. While long-chain phospholipid octadecyl and hexadecyl prodrugs of L-BHDU demonstrated cellular toxicity at concentration of $CC_{50}$ value of 32.5 & 10 µM, respectively. See FIG. 5, Table 1.

Encouraged by the in vitro antiviral data, the inventors then sought to evaluate in vivo antiviral efficacy of these L-BHDU-prodrugs. After the evaluation of the in vitro data of synthesized compounds, due to the higher toxicity and low selectivity of HDP-L-BHDU (compound 6), this compound was dropped from further in vivo testing. In-vivo antiviral efficacy of octadecyl (FIG. 1, Scheme 1, compound 5), POM (FIG. 2, Scheme 2, compound 8), and POC (FIG. 3, Scheme 3, compound 14), prodrugs were compared to L-BHDU in the NuSkin mouse model of VZV replication that employs Athymic Nude mice implanted with adult human skin xenografts. Groups of 10 mice (5 male, 5 female) with skin xenografts were inoculated with VZV-ORF57-Luc, and then treatment was initiated after 3 days via the subcutaneous route. The Vehicle group received only Cremophor-DMSO-saline, and the positive control group received HPMPC (Cidofovir) 10 mg/kg. The test compounds were formulated in CDS at an equimolar concentration to HPMPC, ranging from 11.4 to 24.9 mg/kg based on their molecular weights. Mice were treated once daily on days 3 through 9 post-infections. They were weighed daily and scanned by In Vivo Imaging System (IVIS) on days 3-14 to measure virus spread. The antiviral activity was assessed based on the virus yield measured as a fold increase in Total Flux compared to the value on day 3.

Figure 6:
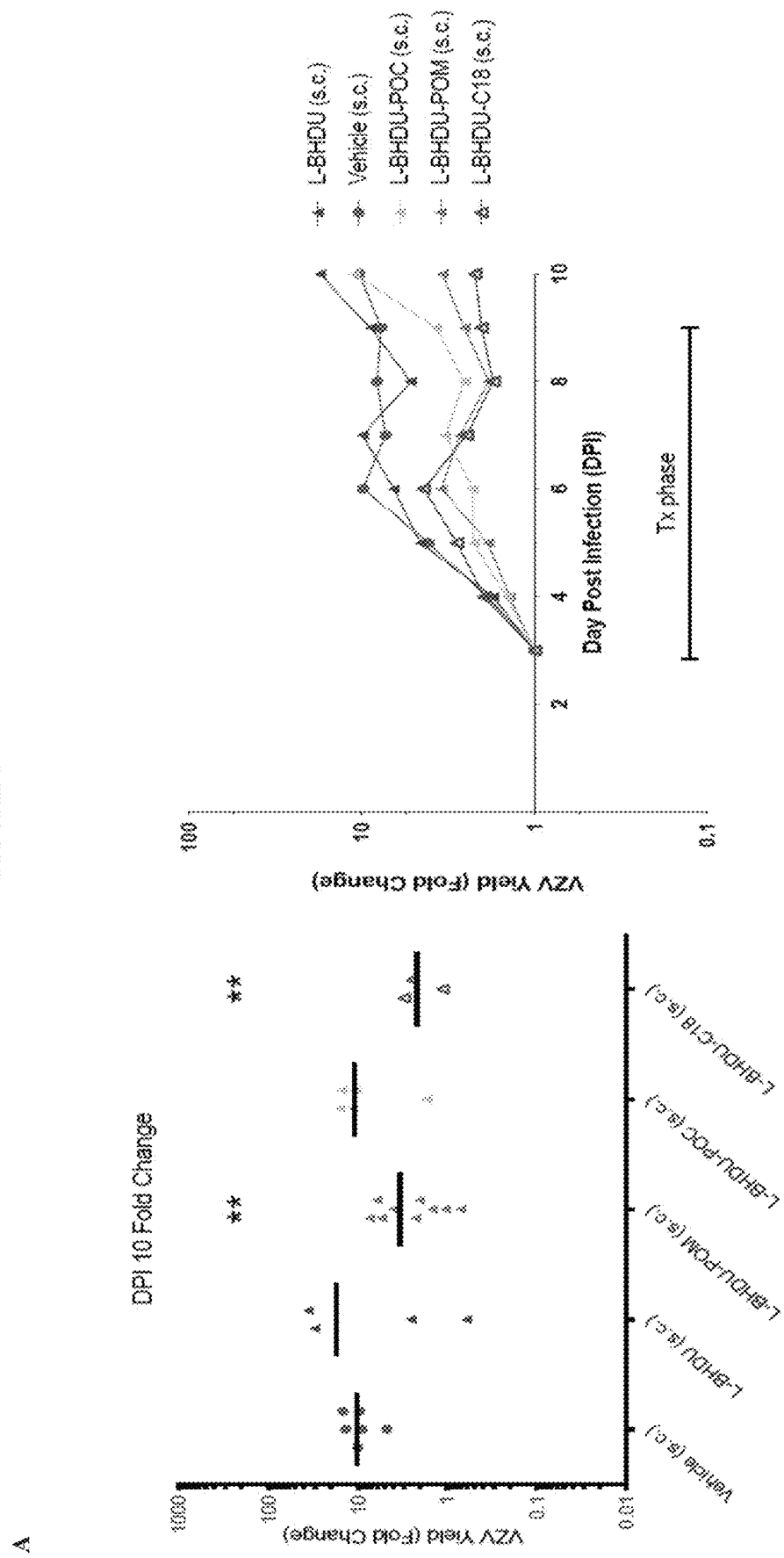
FIG. 6 shows the evaluation of L-BHDU and its OED-L-BHDU (L-BHDU-$C_{18}$), POM-L-BHDU, and POC-L-BHDU, prodrugs in vivo. Mice were treated with vehicle or drugs, and virus yield was measured by bioluminescence imaging. VZV growth rate for individual mice (symbols) and the average for the group (bars) are shown in (A) and (B). Significant reduction in VZV growth rate compared to the vehicle group are indicated both s.c. (A) and p.o. and s.c. (B). The overall significance on day 10 post-inoculation (DPI 10) is p=0.0352 (one-way ANOVA). ** p<0.01 for OED-L-BHDU & POM-L-BHDU and (student's t test with Welch's correction). Cidofovir group (i.p.) has an average fold change of 2-5 on DPI 10. (B).
Figure 6:
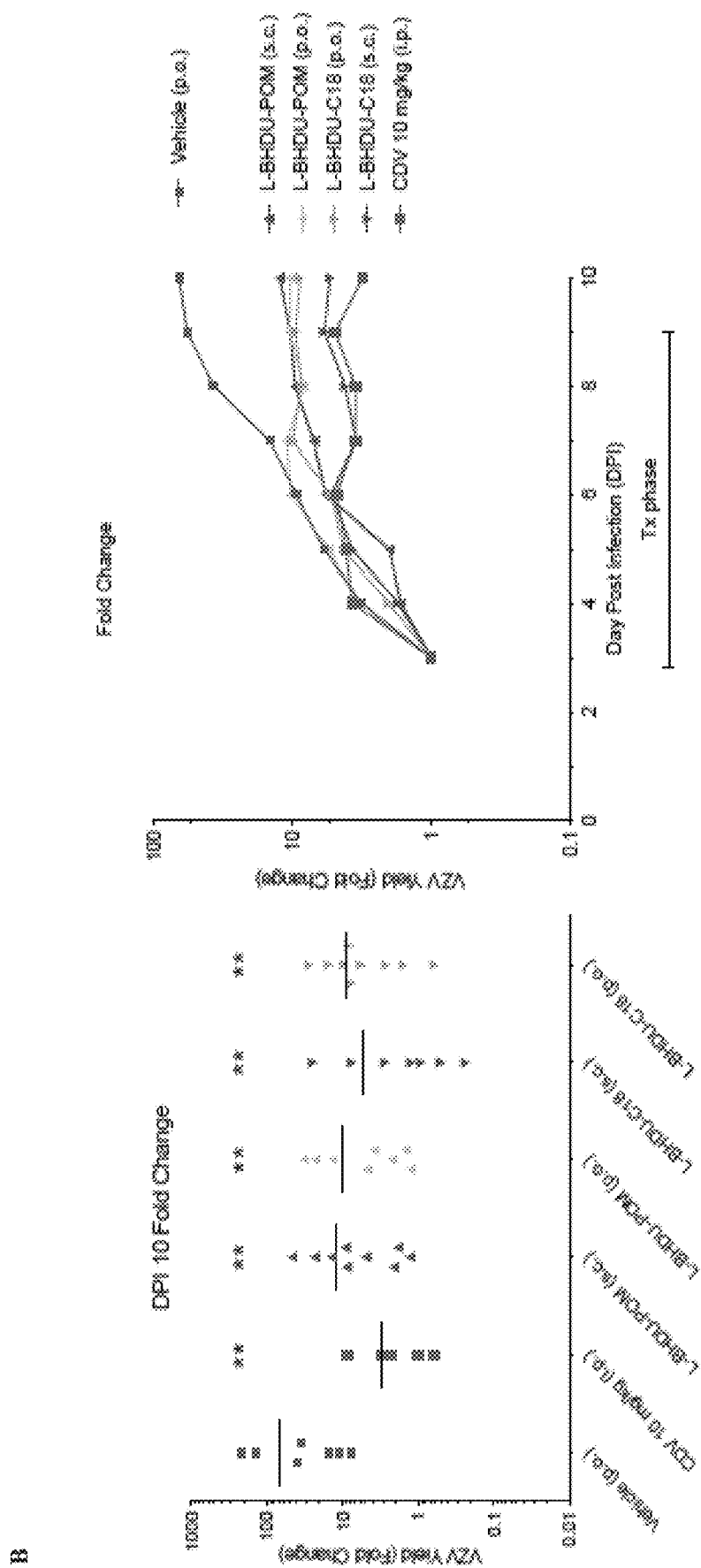
Figure 7:
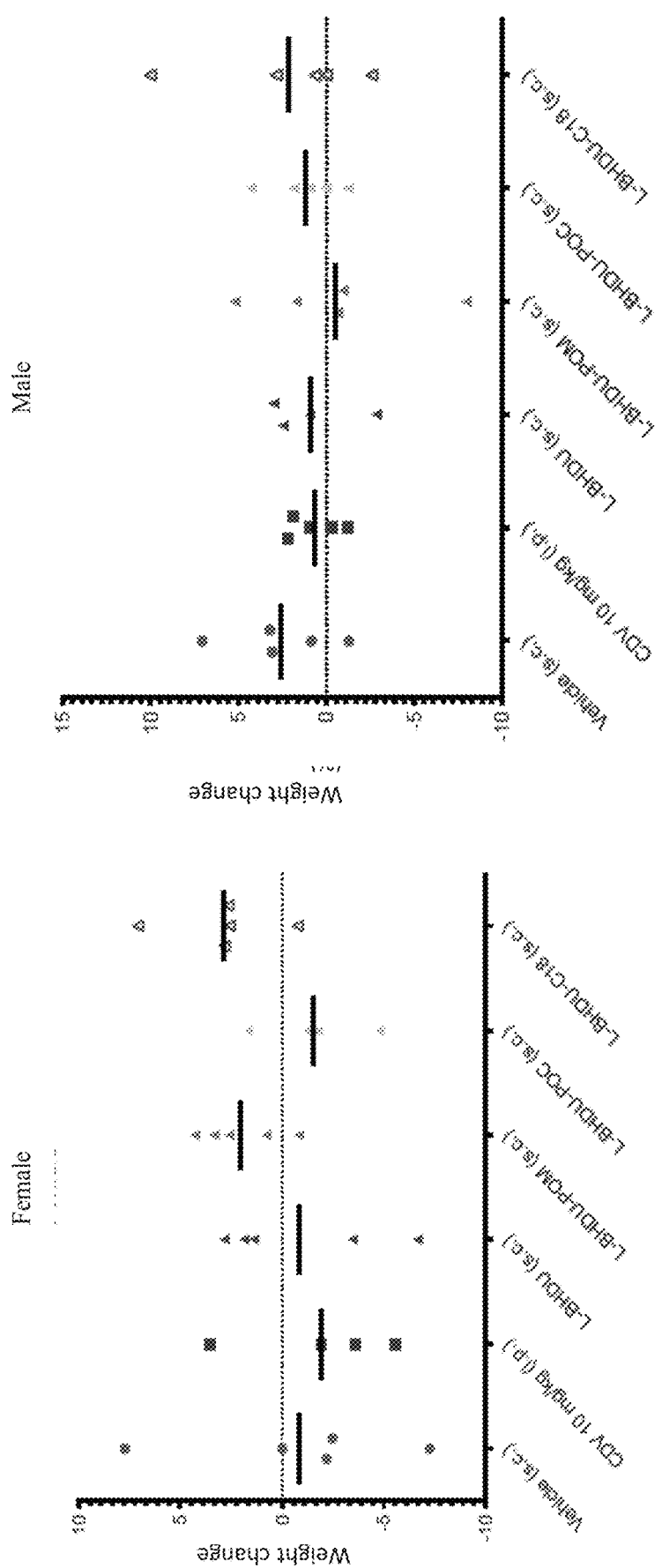
FIG. 7 presents weight change studies which showed that all tested compounds were well tolerated in both male and female mice.

The inventors expected that these prodrug analogs would have antiviral activity based on the previous in vivo assays with L-BHDU. In vivo examination of these derivatives divulged that out of selected prodrug analogs, OED-L-BHDU and POM-L-BHDU have demonstrated superior antiviral potency compared to L-BHDU, without any cellular toxicity. Both prodrugs of L-BHDU were effective in vivo at a dose of around 25 mg/kg/day subcutaneous (s.c.). This is equimolar to cidofovir 10 mg/kg. The parent compound, L-BHDU, and POC-L-BHDU were found ineffective (FIG. 6A). It is worth mentioning that the L-BHDU-POM is also orally equal effective in comparison to cidofovir (ip route, FIG. 6B). It is anticipated that L-BHDU demonstrated less in vivo potency due to its poor pharmacokinetics. However, POC-L-BDHU ester may not be stable enough at the physiological pH to reach an effective concentration inside the cells. This may explain the drop of in vivo effectiveness of POC prodrug. All the tested compounds were also well tolerated by mice (both male and female) and they did not show significant weight loss (FIG. 7).

After these findings OED-L-BHDU (L-BHDU-C18) and (POM-L-BHDU, 37) were selected for the repeated in vivo evaluation with the standard reference cidofovir (10 mg/Kg intravenous route (iv)). In the repeated in vivo studies of L-BHDU-C18 and POM-L-BHDU prodrugs were found more active than the cidofovir via subcutaneous (s.c.) as well as oral (o.p.) route (This is shown in FIG. 6b). POM-L-BHDU and L-BHDU-C18 have shown good in vivo potency, and they have been selected for further study of pharmacokinetic/pharmacodynamic (PK/PD), mechanism of action and toxicological studies. Additionally, evaluation of POM-L-BHDU for the potential interaction with 5-fluorouracil catabolism is also warranted, which is a concern for brivudine but not for L-BHDU.[11] It is envisaged by our preliminary finding that L-BHDU interferes with pyrimidine biosynthesis that is induced by VZV infection in nondividing cells.[22]

Figure 8:
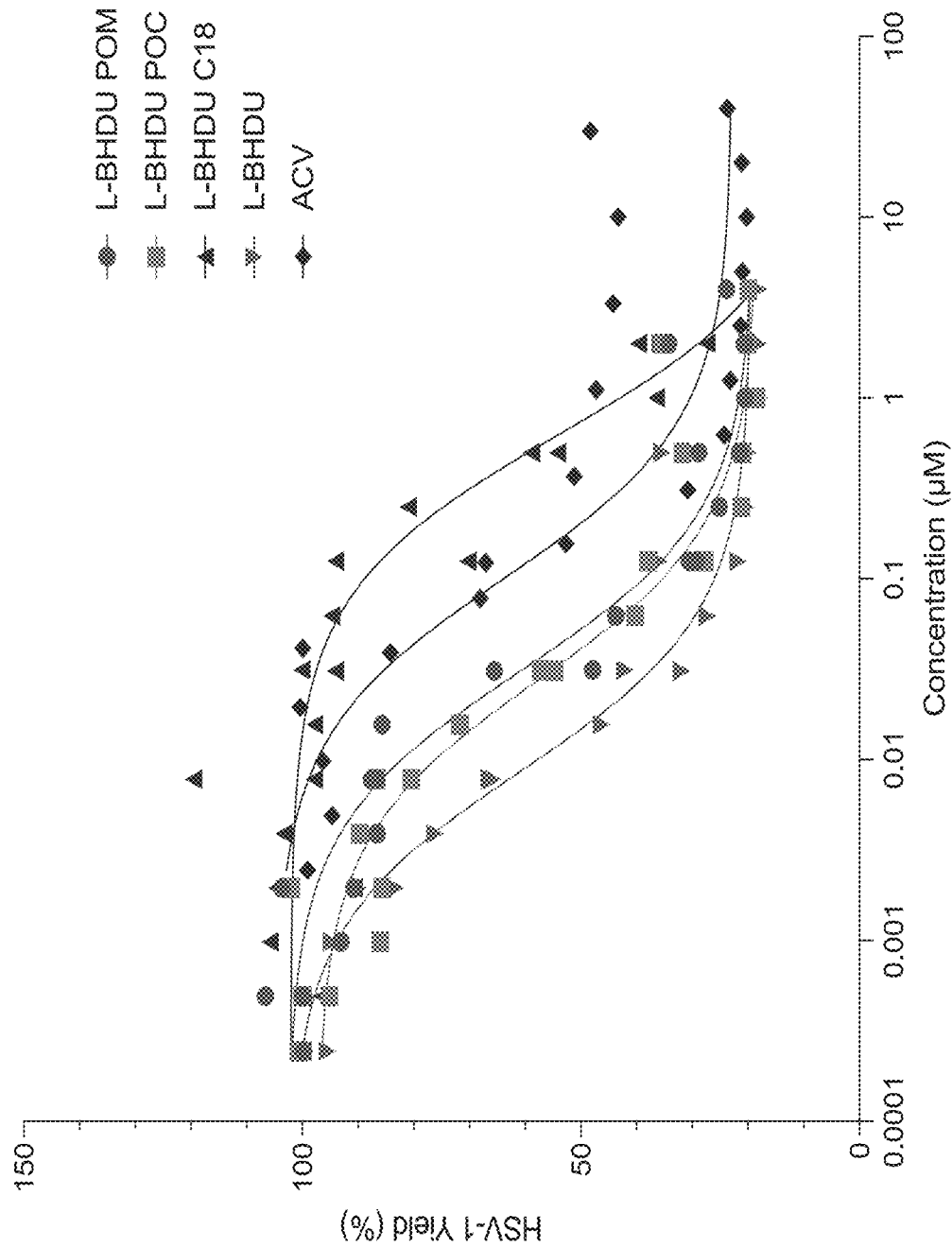
FIG. 8 shows a graph of the anti-HSV-1 activity of L-BHDU prodrugs in Vero Cells.

Additionally, all synthesized compounds were also tested in vitro against herpes simplex viruses (HSV-1, oral herpes) in Vero cells, FIG. 8. L-BHDU and its octadecyl OED-L-BHDU, and POC-L-BHDU prodrugs exhibited good activity against HSV-1. L-BHDU showed an $EC_{50}$ of 0.007 µM with a SI of greater than 12,903 (FIG. 9, Table 2).

POM-L-BHDU expressed $EC_{50}$ of 0.028 µM with SI>3546. However, in contrast, POC-L-BHDU showed more antiviral efficacy $EC_{50}$ of 0.0260 µM with SI>3,846. Octadecyl prodrug was found least potent $EC_{50}$ of 0.7573 µM with a SI of 26.5 in comparison of all synthesized analogs. L-BHDU and its POM and POC prodrugs were found superior to acyclovir ($EC_{50}$=0.0736 µM) without any toxicity $CC_{50}$>100 µM. However, octadecyl prodrug exhibited cellular cytotoxicity at a concentration of 20 µM.

Figure 10:
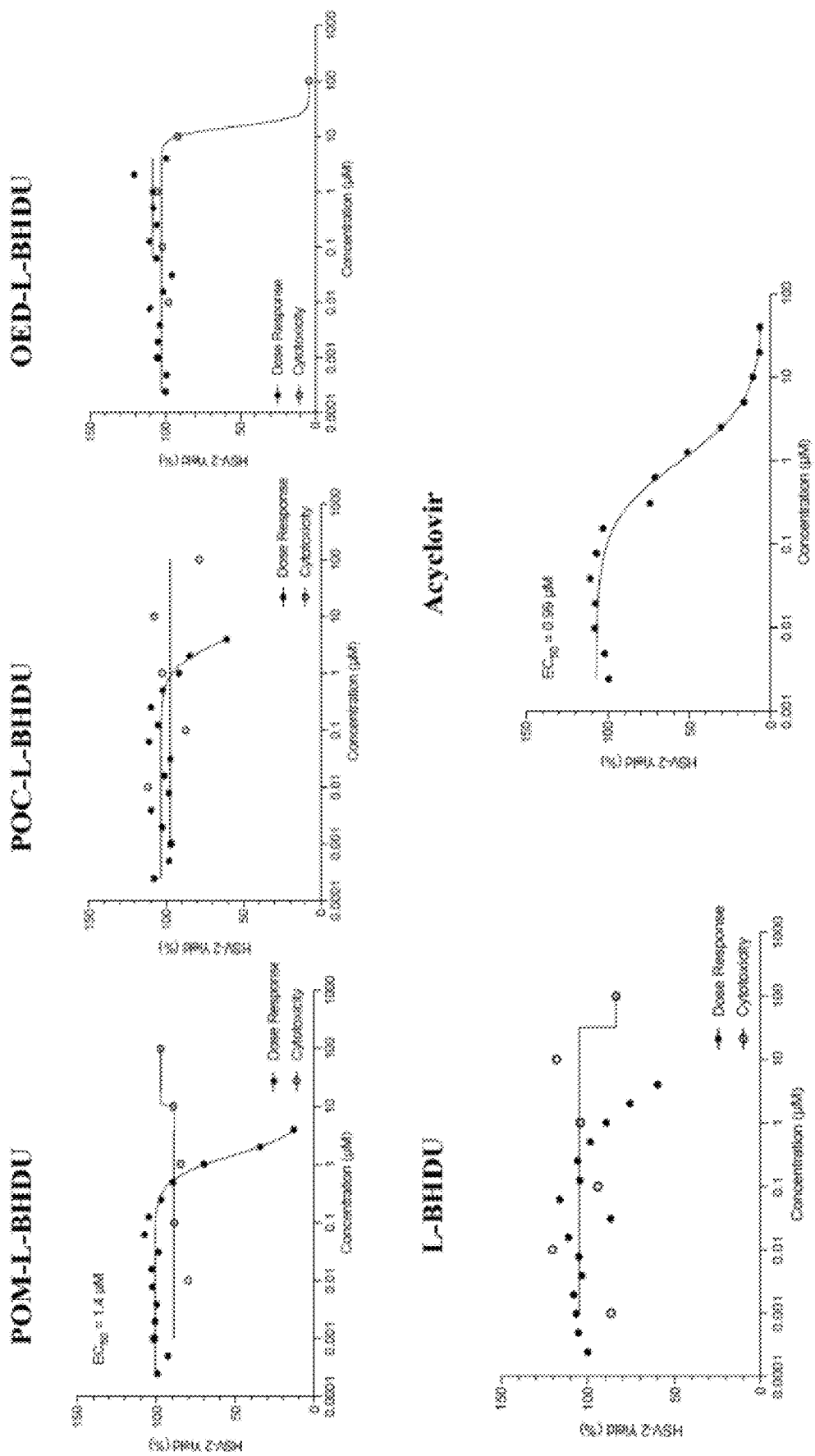
FIG. 10 shows the effect of L-BHDU and its POM, POC & octadecyl prodrugs on HSV-2 replication in the Vero cells in comparison to acyclovir. HSV-2 yield was determined by bioluminescence imaging. Each point represents the mean±standard deviation of a triplicate sample FIG. 11, Table 3 shows L-BHDU, its prodrugs and acyclovir anti-HSV-2 activity in Vero Cells.

Furthermore, antiviral activity of these analogs was tested in vitro against the HSV-2 (genital herpes) in Vero cells using acyclovir as a standard drug reference. It is interesting to report that POM-L-BHDU was only found active against the HSV-2, $EC_{50}$ of 1.4 µM with a SI of >71 (FIG. 10). All other analogs, including L-BDHU, were found ineffective against the HSV-2 (FIG. 11, Table 3). After these findings, it was determined that POM-L-BHDU (37) has potential against the HSV-1 & HSV-2. Further in vivo evaluation of POM prodrug of the L-BDHU will confirm activity. POM prodrug of L-BHDU may demonstrate a superior antiviral HSV-2 efficacy in in vivo mice model.

Figure 12:
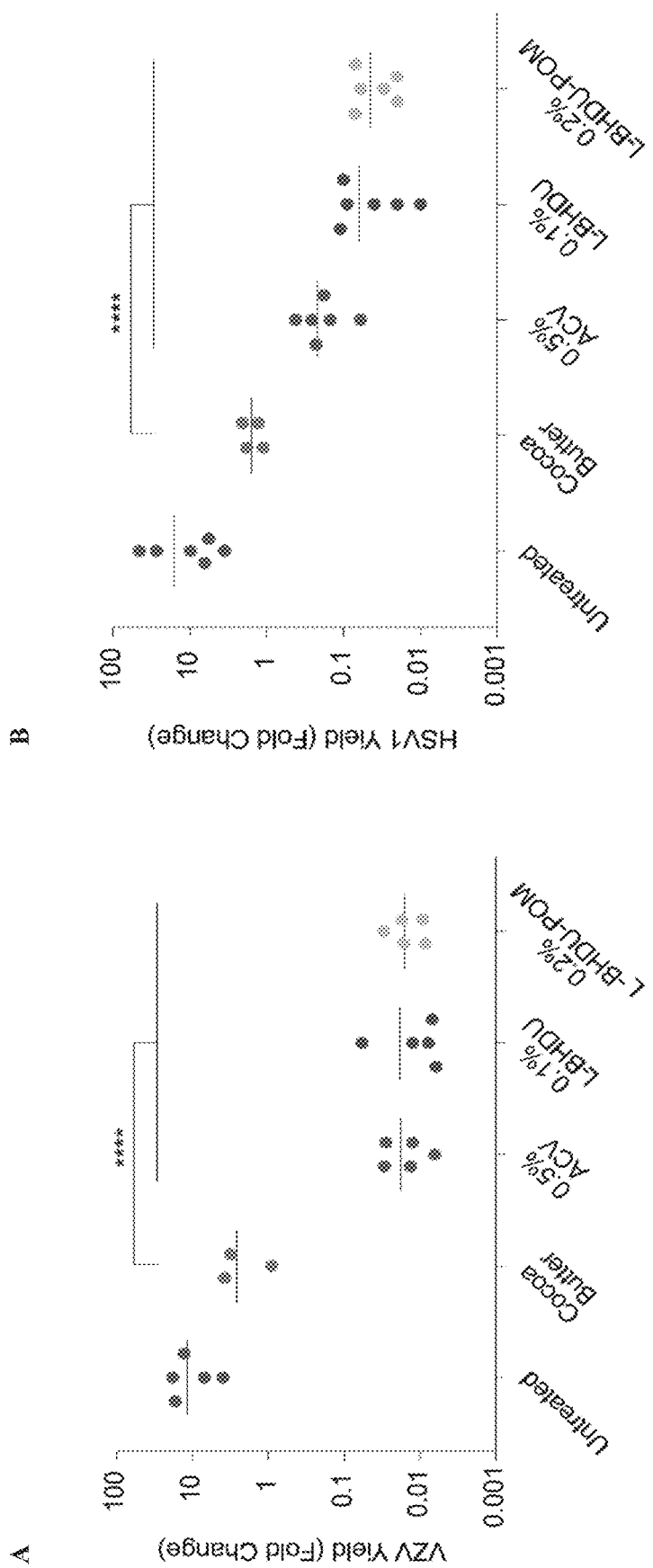
FIG. 12 shows that L-BHDU and its prodrug, L-BHDU-POM, were highly effective at preventing VZV & HSV1 spread in adult human skin. Each compound was formulated in Cocoa Butter and applied topically. POM was formulated in equimolar concentrations to 0.1% L-BHDU. Compounds were not toxic to skin (histology results not shown).

Furthermore POM-L-BHDU was evaluated as a topical treatment for VZV and HSV in a human skin explant model, and it was highly effective against both viruses at 0.2% formulated in cocoa butter (FIG. 12). Importantly, for HSV1, topical L-BHDU-POM 0.2% was more effective than topical acyclovir 0.5% (FIG. 12, right panel).

Figure 13:
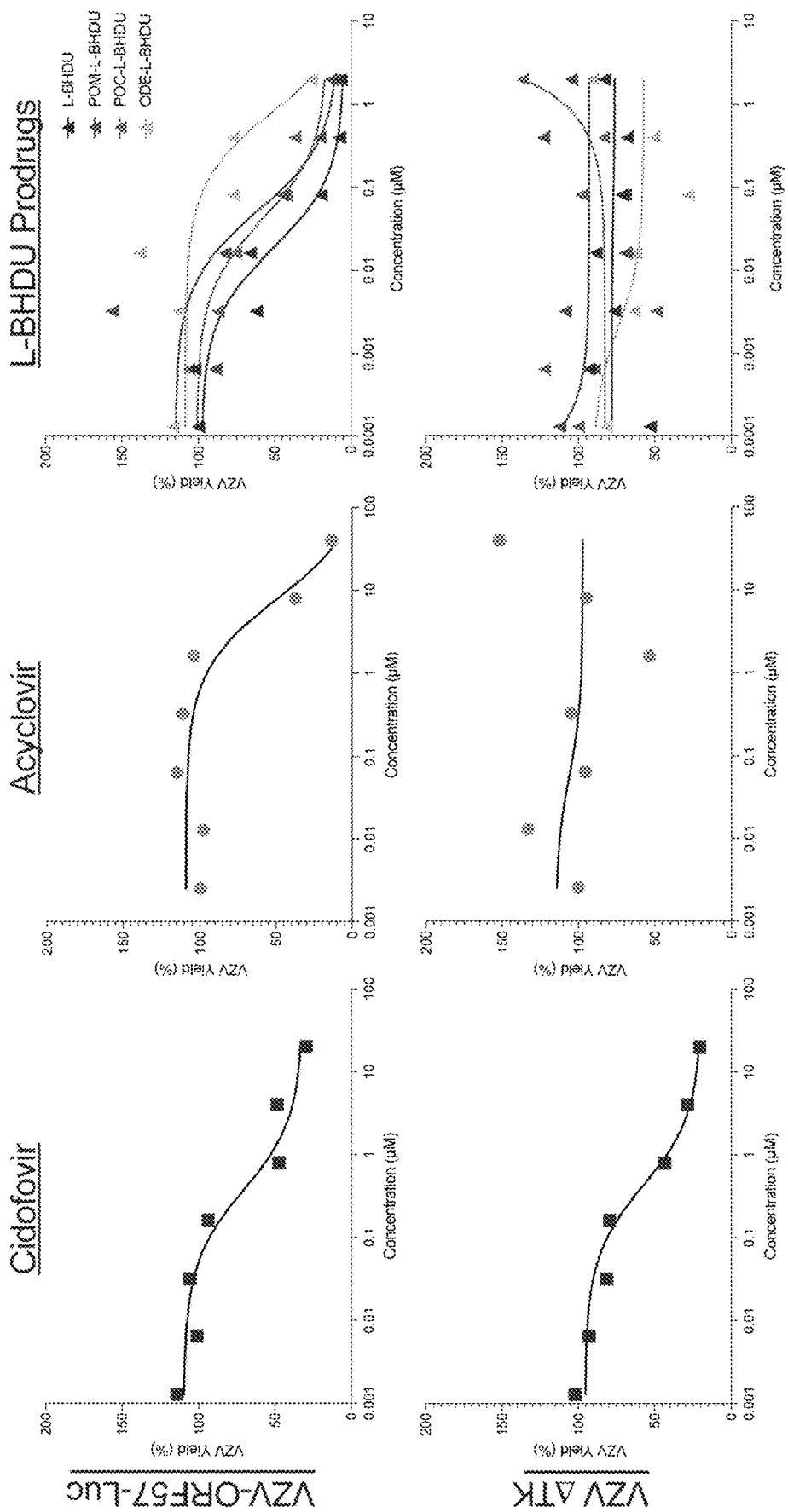
FIG. 13 shows antiviral screening results for L-BHDU and its C18 (ODE-L-BHDU) POM, and POC-L-BHDU against cell-associated VZV-ORF57-Luc, VZV TK-, VZV TS-, and VZV TKTS-. Cidofovir and acyclovir are positive controls. Each symbol represents the average of 6 replicate wells; the line is the best fit curve (error bars omitted for clarity).
Figure 13:
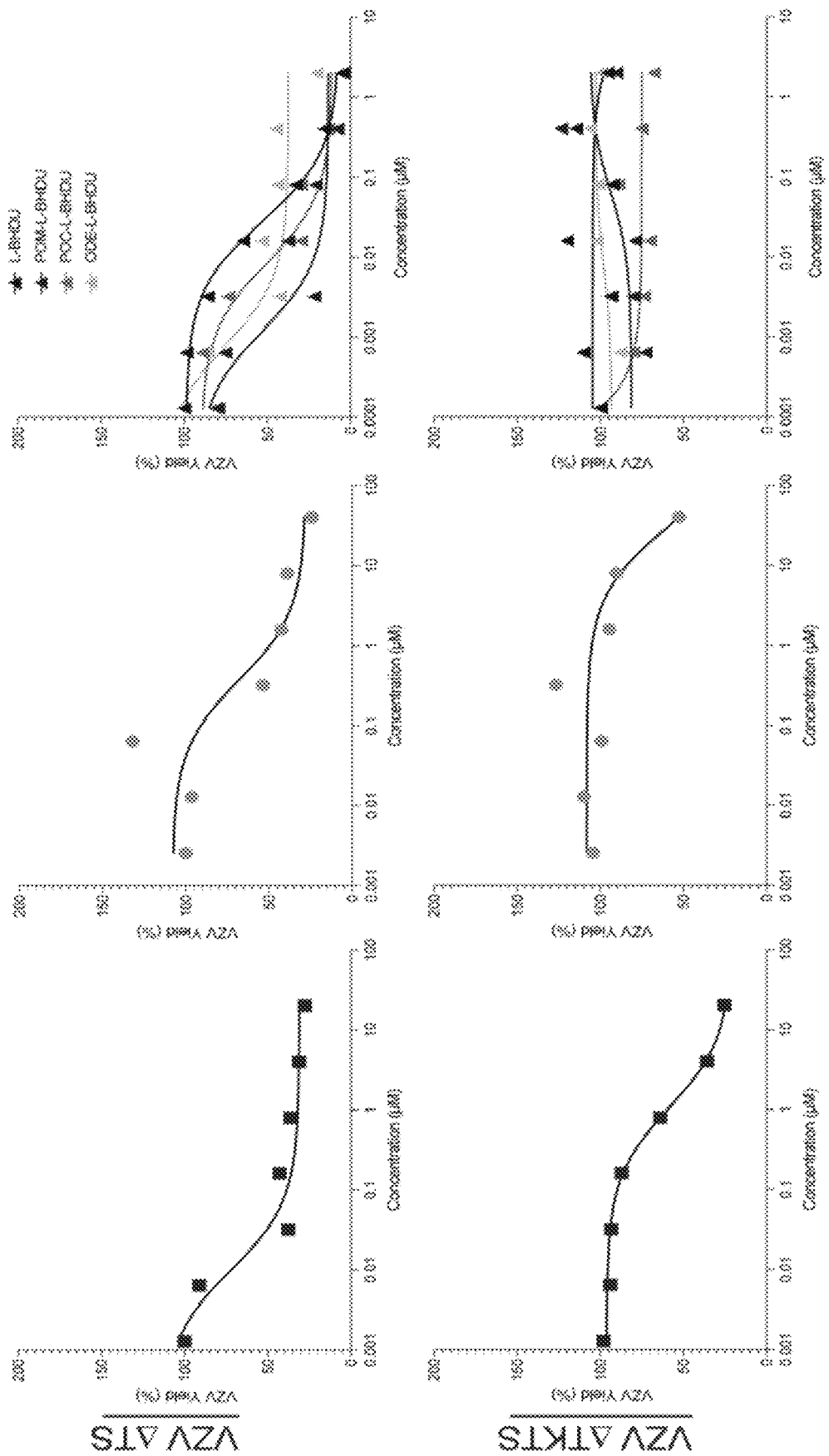

Since L-BHDU, ODE-L-BHDU, POM-L-BHDU and POC-L-BHDU had some of the best antiviral profiles against VZV-ORF57-Luc, the prodrugs were screened against VZV mutants VZV TK (thymidine kinase deficient, —TK), VZV TS (thymidylate synthase deficient, —TS) and VZV TKTS (thymidine kinase and thymidylate synthase deficient, —TKTS) mutants. These studies were performed in the same manner as the efficacy studies described above, except cell-associated VZV-ORF57-Luc, VZV-ORF57-ΔTK, VZV-ORF57-ΔTS and VZV-ORF57-ΔTKTS were used to infect ARPE-19 cells. As before, CDV and ACV were used as positive controls. The $EC_{50}$ for each compound against cell-associated VZV was similar or a little higher than those obtained with cell-free VZV (FIG. 13). In most cases, L-BHDU and its prodrugs were more potent against VZV-ORF57-Luc than CDV or ACV The exception is ODE-L-BHDU, which was less potent compared to CDV but 9-fold more potent compared to ACV (FIG. 14, Table 4).

CONCLUSION

In summary, the inventors have synthesized POM, POC, and long-chain phospholipid prodrugs of L-BHDU. These prodrugs have exhibited significant anti-VZV activity. POM-L-BHDU (8) showed enhanced antiviral potency in comparison to L-BHDU, whereas the OED-L-BHDU (5) and HDP-L-BHDU (6) exhibited lower in vitro activity than the parental molecule against VZV. Furthermore, in vitro potent compound POM-L-BHDU retained its antiviral potency in an in vivo mouse model without cytotoxicity. Moreover, long-chain phospholipid prodrug OED-L-BHDU (compound 5) has also demonstrated significantly enhanced in vivo antiviral activity in comparison to L-BHDU. It was concluded from this study that POM-L-BDHU (8) and OED-L-BHDU (5) should develop as drug candidates against the VZV. Additional biological studies, including anti-VZV activity against drug-resistant mutants, pharmacokinetic studies, molecular mechanism of action studies, tissue distribution studies, are warranted to assess the full potential of these 8 & 9 promising L-BHDU prodrugs. It is noteworthy to mention that all synthesis prodrugs in this study have exhibited good antiviral activity against HSV-1 (oral herpes). POM-L-BDHU (8) also exhibited significant activity against the HSV-2 (genital herpes), while all other prodrug analogs, including L-BDHU, were found inactive against this virus. Overall, POM-L-BDHU (8) and OED-L-BHDU (5) were potent, safe, and well-tolerated, making them a good choice for drug therapy. Also, POM-L-BDHU (8) showed activity consistent with the development of this compound as a good drug candidate against HSV-2 (genital herpes) which is a necessity of current therapeutics.

Experimental Section

General Analytical Methods

Reagents and anhydrous solvents were purchased and used without further purification. Reactions were monitored by thin-layer chromatography plates (TLC silica gel GF 250 microns) that were visualized using a UV lamp (254 nm) and developed with 15% solution of sulfuric acid in methanol. Melting points were recorded on a digital melting point apparatus and are uncorrected. Nuclear magnetic spectra were recorded on 500 MHz for $^1$H NMR, $^{19}$F NMR, 202 MHz for $^{31}$P-NMR and 125 MHz for $^{13}$C NMR with tetramethylsilane (TMS) as an internal standard. Chemical shifts (δ) are quoted as s (singlet), bs (broad singlet), d (doublet), t (triplet), q (quartet), m (multiplet), dd (double doublet) and dt (double triplet). Optical rotations were measured on a digital polarimeter. ESI high resolution mass spectra were recorded on a Q-TOF mass spectrometer. Thin layer chromatography was performed on a glass plate coated with silica gel.

L-BHDU-5'-[(2-octadecyloxyethyl)phosphate] (5). To a solution of 1,2,4-triazole (0.28 g, 4.1 mmol) and triethyl amine (0.57 mL, 4.1 mmol) in anhydrous THE (10 mL) was added to a solution of 2-chlorophenyl dichlorophosphate (2, 0.5 g, 2.0 mmol) in THE (10 mL). The reaction mixture was stirred at rt for 30 min. and then filtered. To the filtrate were added sequentially, addition of 20 mL of THF, L-BHDU (1, 0.49 g, 1.5 mmol) and 1-methylimidazole (0.17 mL, 2.0 mmol). After 1 h, 2-(octadecyloxy)ethanol (0.48 g, 1.5 mmol) was added to mixture and stirred overnight at rt. The solvent was evaporated under reduced pressure and obtained crude was purified by the silica gel column chromatography (3% MeOH/DCM) to produce L-BHDU 5'-[(2-chlorophenyl 2-octadecyloxyethyl) phosphate](3, 0.45 g, 64% yield)$^1$H-NMR (500 MHz, CDCl$_3$) δ 9.13 (bs, 1H, NH), 7.71 (d, J=2.5 Hz, 1H), 7.48-7.38 (m, 3H), 7.20 (t, J=16.0 & 8.5 Hz, 1H), 7.10 (t, J=15.5 & 8.0 Hz, 1H), 6.72 (dd, J=13.5 & 4.5 Hz, 1H); 6.33 (dd, J=16.5 & 7.5 Hz, 1H), 5.17-5.16 (m, 1H), 4.55-4.43 (m, 2H), 4.37-4.32 (m, 2H), 4.22-4.16 (m, 2H), 3.66-3.64 (m, 2H), 3.42 (t, J=13.5 & 8.0 Hz, 2H), 1.52-1.48 (m, 2H), 1.29-1.23 (m, 30H), 0.86 (t, J=14.0 & 7.0 Hz, 3H); $^{31}$P NMR (202 MHz, CDCl$_3$): δ −6.10, −6.36; $^{13}$C-NMR (125 MHz, CDCl$_3$) δ 160.9, 149.3, 146.3, 130.9, 130.5, 128.2, 127.6, 126.6, 126.0, 125.5, 112.1, 110.8, 110.4, 81.5, 81.4, 81.2, 71.5, 71.4, 68.3, 31.9, 29.7, 29.5, 29.4, 26.0, 22.7, 14.2. The obtained intermediate 3 was dissolved in THE and added 0.5N NaOH solution (1.5 mL) at 0° C. The mixture was stirred at 50° C. for 2 h and neutralized with 1N HCl at 0° C. The volatiles were removed under reduced pressure and the residue was purified by silica gel column chromatography (10% MeOH/DCM) to give 5 in 90% yield. Mp 115-117° C.; $^1$H-NMR (500 MHz, DMSO-d$_6$) δ 11.59 (s, 1H), 8.20 (s, 1H), 7.39 (d, J=13.5 Hz, 1H), 7.26 (d, J=14.0 Hz, 1H), 6.18 (d, J=4.5 Hz, 1H), 5.04-5.03 (m, 1H), 4.23 (d, J=9.5 Hz, 1H), 4.08 (t, J=10.0 & 4.5 Hz, 1H), 3.91-3.93 (m, 2H), 3.72-3.69 (m, 2H), 3.43 (t, J=10.0 & 4.5 Hz, 2H), 3.35-3.34 (m, 2H), 1.46-1.43 (m, 2H), 1.28-1.23 (m, 30H), 0.85 (t, J=13.5 & 8.6 Hz, 3H); $^{31}$P NMR (202 MHz, DMSO-d$_6$): δ −1.06; $^{13}$C{$^1$H}NMR (125 MHz, CD$_3$OD) δ 162.3, 150.0, 138.6 (d, J=21.5 Hz), 111.2, 108.3, 107.8, 81.55 (d, J=34.4 Hz), 70.9, 64.6, 46.7, 31.7, 29.4, 29.2, 29.1, 25.8, 22.4, 13.1, 13.0; HRMS (EI) Calcd. For (C$_{30}$H$_{52}$BrN$_2$O$_9$P+Na)$^+$717.2492, found 717.2485.

Compound 6 (50 mg) was synthesized in qualitative yield by following the same procedure as compound 5. Yild 85%; mp 122-123° C.; $^1$H-NMR (500 MHz, CD$_3$OD) δ 8.02 (s, 1H), 7.46 (d, J=14.0 Hz, 1H), 7.04 (d, J=13.5 Hz, 1H), 6.32 (dd, J=7.5 & 1.5 Hz, 1H), 5.19 (s, 1H), 4.29 (dd, J=7.0 & 2.0 Hz, 1H), 4.22-4.19 (m, 1H), 4.15-4.14 (m, 2H), 3.99 (d, J=6.5 & 2.0 Hz, 2H), 3.55 (t, J=13.0 & 7.0 Hz, 2H), 3.43 (t, J=13.0 & 6.5 Hz, 2H), 1.92-1.89 (m, 2H), 1.56-1.52 (m, 2H), 1.37-1.31 (m, 26H), 0.93 (t, J=13.5 & 7.0 Hz, 3H); $^{31}$P NMR (202 MHz, CD$_3$OD): δ 0.58; $^{13}$C{$^1$H}NMR (125 MHz, CD$_3$OD) δ162.3, 150.0, 138.6 (d, J=20.1 Hz), 129.6, 129.1, 111.2, 108.3, 107.8, 104.5, 103.9, 81.5 (d, J=34.6 Hz), 71.1 (d, J=31.5), 70.7, 67.0, 63.6, 62.4, 31.7, 30.8, 30.7, 30.6, 29.4, 29.3, 29.1, 25.9, 22.4, 13.0 (d, J=12.0 Hz); HRMS (EI) Calcd. For (C$_{29}$H$_{50}$BrN$_2$O$_9$P+H)$^+$681.2516 found 681.1507.

Procedure for synthesis of Bis(POM) phosphorylation of L-BHDU: To a stirred solution of L-BHDU (30 mg, 0.094 mmol) and N-methylimidazole (0.61 mL, 0.75 mmol) in dry THE (3 mL), chlorobis(POM) phosphate 7 (154 mg, 0.473 mmol) was added by dissolving in 3 mL of THE at 0° C. and stirred for 15 min. After that reaction was warmed to rt and stirred for 3 h.

Mixture was quenched with methanol and solvent were removed under reduced pressure. The crude was purified by silica gel column chromatography (0.5% MeOH/DCM) to give 8 as a colorless sticky oil (42.0 mg, 71% yield). $^1$H NMR (500 MHz, CDCl$_3$) δ 8.55 (bs, 1H), 7.70 (bs, 1H), 7.43 (d, J=15.0 Hz, 1H), 6.78 (d, J=10.0 Hz, 1H), 6.35 (d, J=10.0 Hz, 1H), 5.71-5.64 (m, 4H), 5.14 (d, J=1.5 Hz, 1H), 4.42-4.30 (m, 2H), 4.25-4.17 (m, 2H), 1.22 (s, 18H); $^{13}$C-NMR (125 MHz, CDCl$_3$) δ 176.8, 160.9, 149.4, 137.3, 128.3, 112.2, 110.6, 102.9, 100.0, 83.1, 81.4, 71.5, 65.1, 38.8, 26.9; $^{31}$P-NMR (202 MHz, CDCl$_3$) δ −3.02, HRMS (EI) Calcd For (C$_{22}$H$_{32}$BrN$_2$O$_{12}$P+H)$^+$627.0954, found m/z 627.0953.

((bis(benzyloxy)phosphoryl)oxy)methyl isopropyl carbonate (10). To a stirred mixture of compound 9 (560 mg, 1.99 mmol) and cesium carbonate (1.6 g, 4.97 mmol) in acetone (10 mL), POC-I (610 mg, 2.38 mmol) was added drop wise at rt and stirred overnight. Reaction mixture was filtered through Buchner funnel and obtained filtrate was concentrated under reduced pressure, obtained residue was purified on silica gel column chromatography (20% EtOAc/hexane) to produce 650 mg of compound 10 as a colorless oil in 82% yield. $^1$H NMR (500 MHz, CDCl$_3$) δ 7.35-7.30 (m, 10H), 5.61-5.58 (d, J=15.0 Hz, 2H), 5.07-5.05 (d, J=10.0 Hz, 4H), 4.90-4.85 (s, 1H), 1.29-1.28 (d, J=5.0 Hz, 6H); $^{31}$P-NMR (202 MHz, CDCl$_3$) δ −2.02

(((benzyloxy)(hydroxy)phosphoryl)oxy)methyl isopropyl carbonate (11). To a stirred solution of compound 10 (1.0 g, 2.54 mmol) in acetonitrile (20 mL), NaI (0.76 g, 5.07 mmol) was added and stirred at 45° C. for 12 h. The reaction mixture was concentrated under reduced pressure and obtained crude was washed with dry ether and dried over high vacuum. After drying residue was used as such for next step without further purification.

((benzoloxyphosphoryl)bis(oxy))bis(methylene) diisopropyl bis(carbonate) (12). To a stirred mixture of compound 11 (231 mg, 0.75 mmol) and cesium carbonate (371 mg, 1.13 mmol) in acetone (10 mL), POC-I (240 mg, 0.98 mmol) was added drop wise at rt and continue stirred for overnight. Reaction mixture was filtered through Buchner funnel and obtained filtrate was concentrated under reduced pressure, residue was purified on silica gel column chromatography (15% EtOAc/hexane) to produce 30 mg of compound 12 as a colorless oil in 70% yield. $^1$H NMR (500 MHz, CDCl$_3$) δ 7.38-7.33 (m, 5H), 5.64-5.62 (d, J=10.0 Hz, 4H), 5.13-5.12 (d, J=5.0 Hz, 2H), 4.94-4.86 (s, 2H), 1.30-1.28 (t, J=10.0 Hz, 6H); $^{31}$P NMR (202 MHz, CDCl$_3$) δ −3.77.

((hydroxyphosphoryl)bis(oxy))bis(methylene) diisopropyl bis(carbonate) (13). To a suspension of compound 12 (300 mg, mmol) and 10% Pd/C (30 mg) in methanol at ambient temperature was treated with H$_2$ at 5 psi for 2 h. The mixture was passed through a celite bed and concentrated under reduced pressure to give 200 mg of 13 as colorless sticky liquid in 85% yield. Compound 13 was used as such for next step reaction without further purification. $^1$H-NMR (500 MHz, CDCl$_3$) δ 7.99 (bs, 1H), 5.63-5.60 (d, J=15.0 Hz, 4H), 4.95-4.88 (s, 2H), 1.31-1.30 (t, J=5.0 & 2.0 Hz, 6H); $^{13}$C-NMR (125 MHz, CDCl$_3$) δ 153.19, 85.46, 73.44, 21.66; $^{31}$P-NMR (202 MHz, CDCl$_3$) δ −3.36.

Bis (POC) prodrug L-BHDU (14) Compound 13 (92 mg, 0.282 mmol) was taken in TEA (1 mL) and pyridine (0.5 mL), stirred at rt for 10 min., then contents were concentrated under reduced pressure followed by co-evaporated with toluene (3 mL). The residue was dissolved in dry THF (3 mL), and cooled to 0° C., after that L-BHDU (30 mg, 0.094) was added, followed by addition of DIPEA (0.05 mL, 0.282 mmol), BOP-Cl (48.0 mg, 0.189 mmol) and 3-nitro-1,2,4-triazole sequentially (21 mg, 0.189 mmol). Mixture was stirred at same temperature for 2 h, diluted with ethyl acetate (50 mL). Organic layer was washed with saturated NaHCO$_3$ solution (20 mL×2), followed by brine solution (10 mL) and dried over Na$_2$SO$_4$. The solvent was removed under reduced pressure and obtained crude was purified by silica gel column chromatography (0.8% Methanol/DCM) to give compound 14 as a colorless sticky solid (13 mg, 22% yield). $^1$H-NMR (500 MHz, CDCl$_3$) δ 8.59 (bs, 1H), 7.69 (s, 1H), 7.44-7.41 (d, J=15.0 MHz, 1H), 6.79-6.76 (d, J=15.0 MHz, 1H), 6.35-6.34 (d, J=5.0 MHz, 1H), 5.71-5.64 (m, 4H), 5.15 (s, 1H), 4.95-4.88 (s, 2H), 4.45-4.35 (m, 2H), 4.33-4.17 (m, 2H), 1.31-1.29 (t, J=15.0 & 7.0 Hz, 6H); $^{13}$C-NMR (125 MHz, CDCl$_3$):160.95, 153.05, 149.4, 137.3, 128.3, 112.2, 110.5, 102.9, 85.8, 81.4, 77.4 73.7, 71.5, 65.2, 21.7; $^{31}$P-NMR (202 MHz, CDCl$_3$) −3.14; HRMS (EI) Calcd for (C$_{20}$H$_{28}$BrN$_2$O$_{14}$P+H)$^+$ 631.0540, found 631.0538.

REFERENCES

1. Gershon, A. A.; Breuer, J.; Cohen, J. I.; Cohrs, R. J.; Gershon, M. D.; Gilden, D.; Grose, C.; Hambleton, S.; Kennedy, P. G. E.; Oxman, M. N.; Seward, J. F.; Yamanishi, K., Varicella zoster virus infection. *Nat Rev Dis Primers* 2015, 1.
2. Marin, M.; Leung, J.; Gershon, A. A., Transmission of Vaccine-Strain Varicella-Zoster Virus: A Systematic Review. *Pediatrics* 2019, 144 (3).
3. Sampathkumar, P.; Drage, L. A.; Martin, D. P., Herpes Zoster (Shingles) and Postherpetic Neuralgia. *Mayo Clin Proc* 2009, 84 (3), 274-280.
4. Field, H. J.; Hodge, R. A. V., Recent developments in anti-herpesvirus drugs. *Brit Med Bull* 2013, 106 (1), 213-249.
5. Lee, M. Y.; Kim, K. S.; Lee, W. K., Intravitreal Foscarnet for the Treatment of Acyclovir-resistant Acute Retinal Necrosis Caused by Varicella Zoster *Virus. Ocul Immunol Inflamm* 2011, 19 (3), 212-213.
6. Andrei, G.; Snoeck, R., Advances and Perspectives in the Management of Varicella-Zoster Virus Infections. *Molecules* 2021, 26 (4).
7. Hoffman, J., Overview of antiviral medications used in ophthalmology. *Community Eye Health.* 2020, 33 (108), 85-88.
8. De Clercq, E., (E)-5-(2-bromovinyl)-2'-deoxyuridine (BVDU). *Med Res Rev* 2005, 25 (1), 1-20.
9. De Clercq, E., Discovery and development of BVDU (brivudin) as a therapeutic for the treatment of herpes zoster. *Biochem Pharmacol* 2004, 68 (12), 2301-2315.
10. Choi, Y.; Li, L.; Grill, S.; Gullen, E.; Lee, C. S.; Gumina, G.; Tsujii, E.; Cheng, Y. C.; Chu, C. K., Structure-activity relationships of (E)-5-(2-bromovinyl) uracil and related pyrimidine nucleosides as antiviral agents for herpes viruses. *J Med Chem* 2000, 43 (13), 2538-2546.
11. De, C.; Liu, D. M.; Zheng, B.; Singh, U. S.; Chavre, S.; White, C.; Arnold, R. D.; Hagen, F. K.; Chu, C. K.; Moffat, J. F., beta-L-1-[5-(E-2-bromovinyl)-2-(hydroxymethyl)-1,3-(dioxolan-4-yl)] uracil (L-BHDU) prevents varicella-zoster virus replication in a SCID-Hu mouse model and does not interfere with 5-fluorouracil catabolism. *Antivir Res* 2014, 110, 10-19.
12. Pradere, U.; Garnier-Amblard, E. C.; Coats, S. J.; Amblard, F.; Schinazi, R. F., Synthesis of Nucleoside Phosphate and Phosphonate Prodrugs. *Chem Rev* 2014, 114 (18), 9154-9218.
13. Naesens, L.; Neyts, J.; Balzarini, J.; Bischofberger, N.; Declercq, E., In-Vivo Antiretroviral Efficacy of Oral Bis (Pom)-Pmea, the Bis(Pivaloyloxymethyl) Prodrug of 9-(2-Phosphonylmethoxyethyl)Adenine (Pmea). *Nucleos Nucleot* 1995, 14 (3-5), 767-770.
14. Marcellin, P.; Chang, T.; Lim, S. G.; Tong, M. J.; Sievert, W.; Shiffman, M. L.; Jeffers, L.; Goodman, Z.; Wulfsohn, M. S.; Xiong, S.; Fry, J.; Brosgart, C. L.; Afdhal, N.; O'Conner, C.; Andreone, P.; Cursaro, C.; Angus, P.; Vaughan, R.; Bain, V.; Gutfreund, K.; Barange, K.; Duffant, M.; Barnes, E.; Bennett, M.; Pressman, J.; Bernstein, D.; Bonino, F.; Coco, B.; Borum, M.; Schuck, S.; Bourliere, M.; Benali, S.; Boyer, N.; Castelnau, C.; Brown, R.; Scales, S.; Buggisch, P.; Peterson, J.; Cooksley, G.; Mac-Donald, G.; Couzigou, P.; Foucner, D.; Crawford, D.; Der, A.; Desmond, P.; Boussioutas, A.; DiBisceglie, A.; Bacon, B.; Dieterich, D.; Goldman, D.; Dusheiko, G.; Enriquez, J.; Gallego, A.; Esposito, S.; Lemieszewski, J.; Esteban, R.; Buti, M.; Faust, T.; Wherity, K.; Francavilla, A.; Malcangi, F.; Fried, M.; Nakayama, C.; Gilson, R.; Lascar, M.; Gish, R.; Trinh, H.; Gordon, S.; Colar, S.; Gregor, M.; Kaiser, S.; Heathcote, I.; Imagawa, D.; Jacobson, I.; Rooney, J.; James, C.; Fallis, R.; Jain, A.; Chen, S.; Ma, J.; Hsing, A.; Nonaka-Wong, S.; Kraus, M.; Jen, C. M.;

Kaita, K.; Koval, G.; Parrish, H.; Kowdley, K.; Kronborg, I.; Nicoll, A.; Kullavanijaya, P.; Amonrattanakosol, J.; Lao-Tan, J.; Garcia, L.; Liaw, Y. F.; Chien, R. N.; Lok, A.; Richtmyer, P.; Luengrojanakul, P.; Tanwandee, T.; Manns, M.; Schueler, A.; Martin, P.; Peacock, V.; McCaughan, G.; Strasser, S.; McHutchison, J.; Pockros, P.; Merican, I.; Lachmanan, S.; Mohamed, R.; Naccarato, R.; Fagiuoli, S.; Nelson, M.; Higgs, C.; Pastore, G.; Perrillo, R.; Denham, C.; Pol, S.; Fontaine, H.; Riely, C.; Litley, D.; Rizzetto, M.; Lagget, M.; Rodriguez, M.; Espiga, M.; Rustgi, V.; Lee, P.; Sacks, S.; Farley, J.; Samuel, D.; Feray, C.; Sasadeusz, J.; Gioupouki, M.; Shaw, D.; Le Mire, M.; Shelton, D.; Sherman, M.; Bartolucci, A.; Schiff, E.; Siebert, A.; Sollano, J.; Dy, F.; Thuluvath, P.; Tong, L.; Trepo, C.; Maynard, M.; Trinchet, J. C.; Carrie, N.; Vetter, D.; Metzger, S.; Vierling, J.; Clarke-Platt, J.; Wakil, E.; Bzowej, N.; Warnes, T.; Wright, T.; Kwong, A.; Young, Y. Y.; Zarski, J. P.; Leroy, V.; Grp, A. D. S.; Grp, R. F. V. H., Adefovir dipivoxil for the treatment of hepatitis B e antigen-positive chronic hepatitis B. *New Engl J Med* 2003, 348 (9), 808-816.
15. Fung, H. B.; Stone, E. A.; Piacenti, F. J., Tenofovir disoproxil fumarate: A nucleotide reverse transcriptase inhibitor for the treatment of HIV infection. *Clin Ther* 2002, 24 (10), 1515-1548.
16. Wiemer, A. J.; Wiemer, D. F., Prodrugs of Phosphonates and Phosphates: Crossing the Membrane Barrier. *Top Curr Chem* 2015, 360, 115-160.
17. Beadle, J. R.; Hartline, C.; Aldern, K. A.; Rodriguez, N.; Harden, E.; Kern, E. R.; Hostetler, K. Y., Alkoxyalkyl esters of cidofovir and cyclic cidofovir exhibit multiple-log enhancement of antiviral activity against cytomegalovirus and herpesvirus replication in vitro. *Antimicrob Agents Ch* 2002, 46 (8), 2381-2386.
18. Liang, Y.; Narayanasamy, J.; Schinazi, R. F.; Chu, C. K., Phosphoramidate and phosphate prodrugs of (−)-beta-D-(2R,4R)-dioxolane-thymine: synthesis, anti-HIV activity and stability studies. *Bioorg Med Chem* 2006, 14 (7), 2178-89.
19. Hwang, Y. S.; Cole, P. A., Efficient synthesis of phosphorylated prodrugs with bis(POM)-phosphoryl chloride. *Org Lett* 2004, 6 (10), 1555-1556.
20. De, C.; Liu, D.; Singh, U. S.; Chu, C. K.; Moffat, J. F., β-L-1-[5-(E-2-Bromovinyl)-2-(Hydroxymethyl)-1,3 Dioxolan-4-yl)] Uracil (L-BHDU) Inhibits Varicella Zoster Virus Replication by Depleting the Cellular dTTP Pool. *bioRxiv* 2020, 02.13.948216.
21. De, C.; Liu, D.; Depledge, D.; Breuer, J.; Singh, U. S.; Hartline, C.; Prichard, M. N.; Chu, C. K.; Moffat, J. F., β-L-1-[5-(E-2-Bromovinyl)-2-(hydroxymethyl)-1,3-dioxolan-4-yl)] uracil (L-BHDU) effectiveness against varicella-zoster virus and herpes simplex virus type 1 depends on thymidine kinase activity. *bioRxiv* 2020, 02.13.948190.

What is claimed:

1. A prodrug compound of L-BHDU according to the chemical structure I:

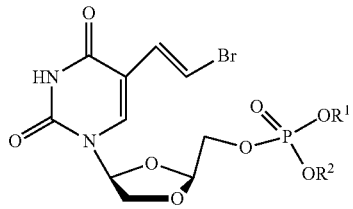

Where $R^1$ is a —$(CH_2)_n$—O—$R^{1a}$ group or a —$(CH_2)_j$—O—$C(O)O_k$—$R^{2a}$ group;
$R^2$ is H, a —$(CH_2)_n$—O—$R^{1a}$ group or a —$(CH_2)_j$—O—$C(O)O_k$—$R^{2a}$ group;
$R^{1a}$ is independently a $C_6$-$C_{30}$ alkyl group, often a $C_{12}$-$C_{22}$ alkyl group, often a $C_{14}$-$C_{20}$ alkyl group or a $C_{16}$-$C_{18}$ alkyl group, often a $C_{16}$ or $C_{18}$ alkyl group;
$R^{2a}$ is independently a $C_1$-$C_{12}$ alkyl group, often a $C_2$-$C_6$ alkyl group, a $C_3$-$C_4$ alkyl group, an isopropyl, t-butyl or sec-butyl group, or an isopropyl or t-butyl group;
Each j is independently 1-6, 1-3, often 1 or 2;
Each k is 0 or 1;
Each n is independently 1-6; or
A pharmaceutically acceptable salt, solute or polymorph thereof.

2. The compound according to claim 1 wherein $R^1$ is a —$(CH_2)_n$—O—$R^{1a}$ group and n is 2 or 3.

3. The compound according to claim 2 wherein $R^{1a}$ is a $C_{14}$-$C_{20}$ alkyl or $C_{16}$-$C_{18}$ alkyl group and n is 2 or 3.

4. The compound according to claim 3 wherein $R^{1a}$ is $C_{16}$ or $C_{18}$ and $R^2$ is H.

5. The compound according to claim 4 wherein $R^{1a}$ is $C_{18}$ and n is 2.

6. The compound according to claim 4 wherein $R^{1a}$ is $C_{16}$ and n is 2.

7. The compound according to claim 1, wherein $R^1$ is a —$(CH_2)_n$—O—$R^{1a}$ group and $R^2$ is H or —$(CH_2)_n$—O—$R^{1a}$.

8. The compound according to claim 1 wherein $R^1$ is a $(CH_2)_j$—O—$C(O)O_k$—$R^{2a}$ group and $R^2$ is H or a —$(CH_2)_j$—O—$C(O)O_k$—$R^{2a}$ group.

9. The compound according to claim 8 wherein $R^2$ is a —$(CH_2)_j$—O—$C(O)O_k$—$R^{2a}$ group and j is 1-4.

10. The compound according to claim 9 wherein j is 1 or 2 and $R^{2a}$ is a $C_1$-$C_{12}$ alkyl group.

11. The compound according to claim 10 wherein j is 1 or 2 and $R^{2a}$ is a $C_2$-$C_6$ alkyl group.

12. The compound according to claim 11 wherein j is 1 and $R^{2a}$ is a $C_3$ or $C_4$ alkyl group.

13. The compound according to claim 11 wherein j is 2 and $R^{2a}$ is a $C_3$ or $C_4$ alkyl group.

14. The compound according to claim 1 wherein $R^1$ is —$(CH_2)_j$—O—$C(O)O_k$—$R^{2a}$.

15. The compound according to claim 14 wherein j is 1.

16. The compound according to claim 15 wherein k is 0.

17. The compound according to claim 15 wherein k is 1.

18. The compound according to claim 8 wherein $R^1$ and $R^2$ are the same.

19. A compound according to the chemical structure:

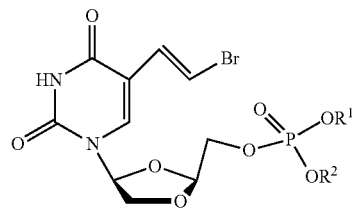

Wherein $R^1$ is a —$(CH_2)_n$—O—$R^{1a}$ group, n is 2 or 3, $R^{1a}$ is a $C_{16}$ or $C_{18}$ alkyl group and $R_2$ is H, or a pharmaceutically acceptable salt, solvate or polymorph thereof.

20. The compound according to claim 19 wherein n is 2 and $R^{1a}$ is a $C_{18}$ alkyl group.

21. The compound according to claim 19 wherein n is 3 and $R^{1a}$ is a $C_{16}$ alkyl group.

22. A compound according to the chemical structure:

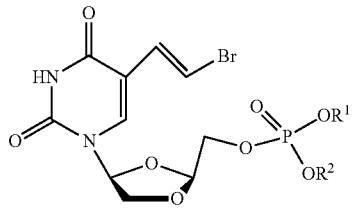

Wherein $R^1$ and $R^2$ are each a —$(CH_2)_j$—O—C(O)O$_k$—$R^{2a}$ group;

$R^{2a}$ is independently an isopropyl or a t-butyl group;

Each j is independently 1 or 2;

Each k is 0 or 1; or

A pharmaceutically acceptable salt, solute or polymorph thereof.

23. The compound according to claim 22 wherein $R^1$ and $R^2$ are identical, j is 1, k is 1 and $R^{2a}$ is an isopropyl group.

24. The compound according to claim 22 wherein $R^1$ and $R^2$ are identical, j is 1, k is 0 and $R^{2a}$ is a tert-butyl group.

25. A pharmaceutical composition comprising an effective amount of a compound according to claim 1 in combination with a pharmaceutically acceptable carrier, additive or excipient.

26. The composition according to claim 25 further including an additional bioactive agent.

27. The composition according to claim 26 wherein said bioactive agent is acyclovir, brivudine, foscarnet, cidofovir (CDV), valacyclovir, famciclovir, zoster-immune globulin (ZIG), vidarabine or a mixture thereof.

28. The composition according to claim 26 wherein said bioactive agent is 5-fluoro uracil.

29. The composition according to claim 27 wherein said bioactive agent is foscarnet, cidovovir or a mixture thereof.

30. A method of treating a viral infection in a patient in need comprising administering to said patient an effective amount of a composition according to claim 25, wherein the viral infection is a varicella zoster virus (VZV) infection, a herpes simplex virus I (HSV-1) infection or a herpes simplex virus II (HSV-2) infection.

31. The method according to claim 30 wherein said virus infection is a VZV infection.

32. The method according to claim 31 wherein said virus infection is caused by wild type VZV or mutant VZV (TK-, TS- or TK-TS-).

33. The method according to claim 30 wherein said virus infection is a HSV-1 infection.

34. The method according to claim 30 wherein said virus infection is a HSV-2 infection.

35. A method of treating a viral infection in a patient in need comprising administering to said patient an effective amount of a compound according to claim 1, wherein the viral infection is a varicella zoster virus (VZV) infection, a herpes simplex virus I (HSV-1) infection or a herpes simplex virus II (HSV-2) infection.

36. The method according to claim 35 wherein said compound is

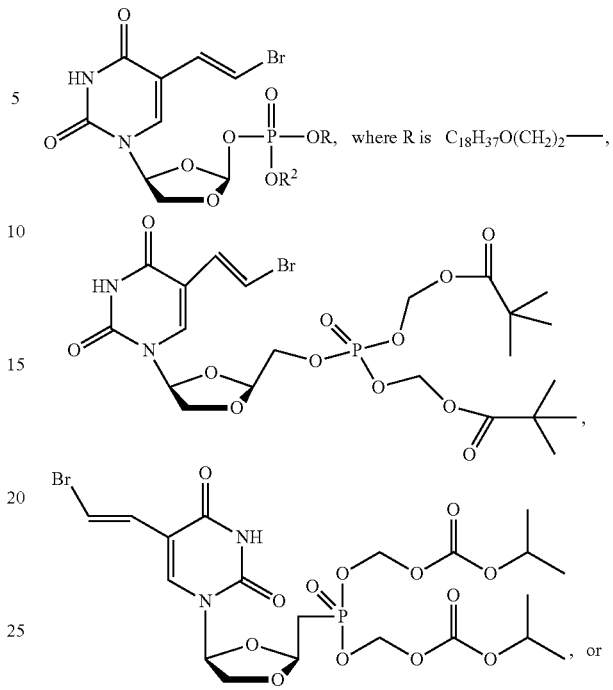

A pharmaceutically acceptable salt thereof.

37. A method of reducing the likelihood of a viral infection in a patient in need comprising administering to said patient an effective amount of a composition according to claim 25, wherein the viral infection is a varicella zoster virus (VZV) infection, a herpes simplex virus I (HSV-1) infection or a herpes simplex virus II (HSV-2) infection.

38. The method according to claim 37 wherein said virus infection is a VZV infection.

39. The method according to claim 37 wherein said virus infection is a HSV-1 infection.

40. The method according to claim 37 wherein said virus infection is a HSV-2 infection.

41. A method of inhibiting or resolving complications of a VZV infection in a patient or subject in need, wherein said complications are postherpetic neuralgia, zoster multiplex, myelitis, herpes ophthalmicus, or zoster sine herpete, the method comprising administering a compound according to claim 1 to said patient or subject in need.

42. The method according to claim 41 wherein said compound is

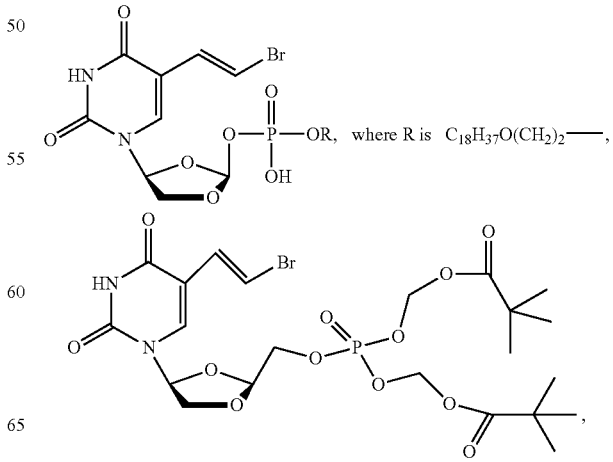

-continued
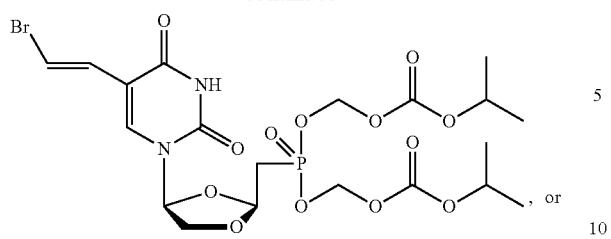
A pharmaceutically acceptable salt thereof.
* * * * *